(12) United States Patent
Son et al.

(10) Patent No.: US 10,786,196 B2
(45) Date of Patent: Sep. 29, 2020

(54) DISPLAY APPARATUS AND CONTROL METHOD THEREOF FOR SKIN CARE ANALYSIS

(71) Applicant: SAMSUNG ELECTRONICS CO., LTD., Suwon-si, Gyeonggi-do (KR)

(72) Inventors: Joo-young Son, Yongin-si (KR); Jae-jin Kim, Ansan-si (KR); Ji-yun Kim, Suwon-si (KR); Dae-young Hyun, Suwon-si (KR); Sun-ah Kim, Seongnam-si (KR); Ga-hyun Joo, Suwon-si (KR); Tae-hwa Hong, Seoul (KR); Hong-il Kim, Yongin-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 179 days.

(21) Appl. No.: 15/214,656

(22) Filed: Jul. 20, 2016

(65) Prior Publication Data

US 2017/0061609 A1 Mar. 2, 2017

(30) Foreign Application Priority Data

Sep. 2, 2015 (KR) .......................... 10-2015-0124138

(51) Int. Cl.
*G06F 16/54* (2019.01)
*G06F 16/583* (2019.01)
(Continued)

(52) U.S. Cl.
CPC ............ *A61B 5/441* (2013.01); *A61B 5/6898* (2013.01); *A61B 5/7425* (2013.01); *G06F 16/54* (2019.01);
(Continued)

(58) Field of Classification Search
CPC ..... G06T 7/0012; A61B 5/441; A61B 5/7425; A61B 5/6898; G06F 19/00; G06F 19/03;
(Continued)

(56) References Cited

U.S. PATENT DOCUMENTS 9,779,167 B2 * 10/2017 Kusumoto ......... G06Q 30/0631
10,361,004 B2 * 7/2019 Pai ....................... A61B 5/6898
(Continued)

FOREIGN PATENT DOCUMENTS

| CN | 103989454 A | 8/2014 |
|----|-------------|--------|
| KR | 10-2012-0092889 | 8/2012 |
| WO | 2014/072375 | 5/2014 |

OTHER PUBLICATIONS

Search Report and Written Opinion dated Dec. 13, 2016 in counterpart International Patent Application No. PCT/KR2016/009768.
(Continued)

*Primary Examiner* — Nicholas Klicos
(74) *Attorney, Agent, or Firm* — Nixon & Vanderhye P.C.

(57) ABSTRACT

A display apparatus includes a display which displays a screen including a plurality of photo contents containing a user face and a processor configured to control the display to distinguishably display the plurality of photo contents based on a photographing time of the plurality of photo contents with reference to a time at which a preset event related with skin has occurred.

18 Claims, 34 Drawing Sheets

(51) Int. Cl.
*A61B 5/00* (2006.01)
*G06T 11/60* (2006.01)
*G16H 30/40* (2018.01)
*G06Q 30/02* (2012.01)
*G06Q 30/06* (2012.01)
*G16H 20/70* (2018.01)

(52) U.S. Cl.
CPC ....... *G06F 16/583* (2019.01); *G06Q 30/0251* (2013.01); *G06Q 30/0641* (2013.01); *G06T 11/60* (2013.01); *G16H 20/70* (2018.01); *G16H 30/40* (2018.01)

(58) Field of Classification Search
CPC ........ G06F 17/30274; G06F 17/30247; G06Q 30/02
See application file for complete search history.

(56) References Cited

U.S. PATENT DOCUMENTS

| | | | |
|---|---|---|---|
| 2003/0065526 A1 | 4/2003 | Giacchetti et al. | |
| 2004/0170337 A1* | 9/2004 | Simon | G06K 9/00234 382/254 |
| 2006/0036949 A1* | 2/2006 | Moore | G06F 3/0482 715/730 |
| 2006/0129411 A1* | 6/2006 | Bhatti | G06Q 30/02 705/346 |
| 2006/0280497 A1 | 12/2006 | Wakabayashi | |
| 2007/0058858 A1* | 3/2007 | Harville | A45D 44/005 382/165 |
| 2007/0064979 A1* | 3/2007 | Chhibber | G06K 9/00288 382/118 |
| 2008/0267458 A1* | 10/2008 | Laganiere | G06K 9/00221 382/118 |
| 2009/0136101 A1* | 5/2009 | Chhibber | A61B 5/442 382/128 |
| 2009/0245603 A1* | 10/2009 | Koruga | A45D 44/00 382/128 |
| 2009/0304243 A1* | 12/2009 | Mertz | A61B 5/444 382/128 |
| 2010/0185064 A1* | 7/2010 | Bandic | A61B 5/0059 600/306 |
| 2011/0007975 A1* | 1/2011 | Kazama | G06K 9/00234 382/225 |
| 2011/0043643 A1* | 2/2011 | Yu | H04N 1/00209 348/207.1 |
| 2011/0213253 A1* | 9/2011 | Kruglick | A61B 5/0064 600/477 |
| 2012/0078088 A1* | 3/2012 | Whitestone | A61B 5/0077 600/425 |
| 2012/0157821 A1 | 6/2012 | Kitamura et al. | |
| 2012/0224769 A1* | 9/2012 | White | G06K 9/00362 382/165 |
| 2013/0058543 A1* | 3/2013 | Thomas | A45D 44/005 382/118 |
| 2013/0301925 A1* | 11/2013 | Nashida | G06T 11/60 382/195 |
| 2014/0121188 A1* | 5/2014 | Tamarkin | A61K 47/10 514/152 |
| 2014/0176764 A1 | 6/2014 | Nakamura et al. | |
| 2014/0304629 A1* | 10/2014 | Cummins | A61B 5/742 715/764 |
| 2014/0330130 A1 | 11/2014 | Arneberg et al. | |
| 2015/0261996 A1* | 9/2015 | Kim | G06K 9/00255 348/14.03 |
| 2016/0125228 A1* | 5/2016 | Son | G06F 19/345 382/118 |
| 2016/0162728 A1* | 6/2016 | Arai | A61B 5/743 382/118 |
| 2017/0076444 A1* | 3/2017 | Petit | A61B 5/441 |
| 2017/0231550 A1* | 8/2017 | Do | G06T 7/11 382/128 |

OTHER PUBLICATIONS

Extended European Search Report for EP Application No. 16842307.7 dated Jul. 13, 2018.
Chinese Office Action dated Sep. 3, 2019 for CN Application No. 201680050978.6.
India First Examination Report dated Jun. 24, 2020 for India Application No. 201817006978.

* cited by examiner

100

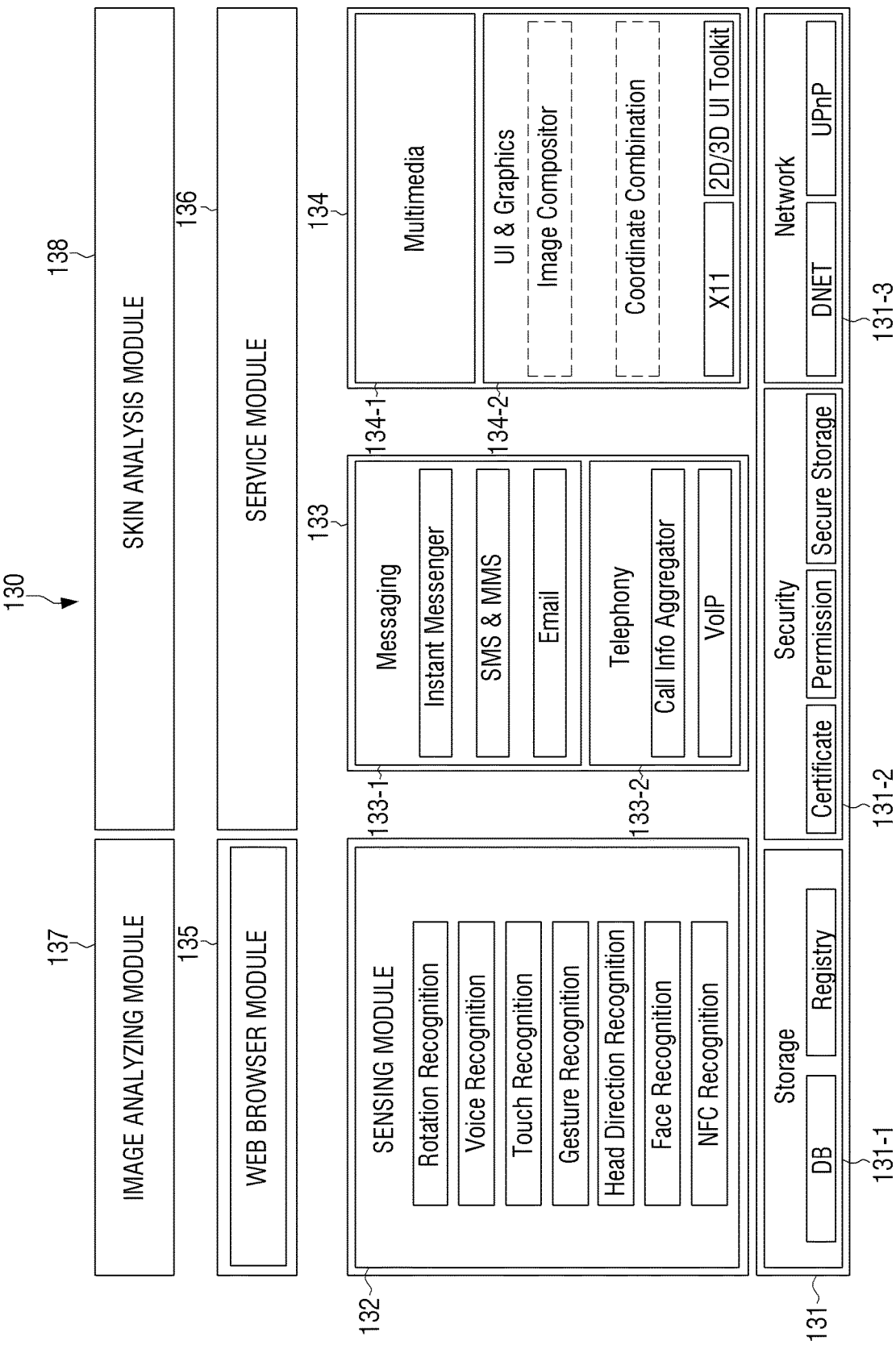

DISPLAY APPARATUS AND CONTROL METHOD THEREOF FOR SKIN CARE ANALYSIS

CROSS-REFERENCE TO RELATED APPLICATIONS

This application is based on and claims priority under 35 U.S.C. § 119 to Korean Patent Application No. 10-2015-0124138, filed on Sep. 2, 2015 in the Korean Intellectual Property Office, the disclosure of which is incorporated by reference herein in its entirety.

BACKGROUND

1. Field

Devices and methods consistent with what is disclosed herein relate to a display apparatus and a control method thereof, and more specifically, to a display apparatus configured to photograph a photo and a control method thereof.

2. Description of Related Art

With the development of electronic technology, various types of display apparatuses are developed. Specifically, the display apparatuses such as TVs, PCs, laptop computers, tablet PCs, cellular phones, MP3 players, and so on show high distribution rate such that most families use such apparatuses.

Recently, efforts to further develop the display apparatuses to newer forms have been made in order to satisfy the user needs demanding new and various functions. For example, various services using a camera on a user terminal apparatus such as smart phone are provided.

SUMMARY

Example embodiments address certain disadvantages in the art.

According to an example embodiment, a display apparatus allowing easy comparison of skin conditions before and after a skin-related event, by distinguishing skin-analyzed photo content with reference to a time at which the skin-related event is occurred and providing the result, and a control method thereof are provided.

According to an example embodiment, the display apparatus includes a display configured to display a screen including a plurality of photo contents containing a user face, and a processor configured to control the display to distinguishably display the plurality of photo contents based on a photographing time of the plurality of photo contents with reference to a time at which a preset event has occurred.

The display apparatus may additionally include a user interface configured to receive an input of a user command. When, in response to the received user command, a first photo content is selected among the photo contents photographed before the time at which the preset event occurred, and a second photo content is selected among the photo contents photographed after the time at which the preset event occurred, the processor may be configured to provide a user interface (UI) screen to compare skin conditions of the user face contained in each of the selected first and second photo content.

The processor may be configured to display a graphic user interface (GUI) indicating the preset event between the photo contents photographed before and after the in time at which the preset event occurred so as to distinguishably display the plurality of photo contents with reference to the time at which the preset event occurred.

The display apparatus may additionally include a user interface configured to receive the input of a user command. When the GUI is selected based on the user command, the processor may be configured to select a third photo content among the photo contents photographed before the time at which the preset event occurred, to select a fourth photo content having a photographing condition similar to that of the third photo content among the photo contents photographed after the time at which the preset event occurred, and to provide a UI screen to compare the skin conditions of the user faces respectively contained in the selected third and fourth photo content.

The photographing condition may include at least one of a face size, a face angle, a face expression, make-up or no make-up, presence or absence of accessory, and photographing lighting.

The preset event related with skin may include at least one of a skin care event, a skin treatment event, a product purchasing event related with skin, an event related with a change of location influencing the skin, an event related with weather influencing the skin, an event related with food consumption influencing the skin, and a holiday event.

The processor may be configured to determine the preset event based on at least one of a skin-related event input on a preset calendar, a skin-related event comprised in a text message, GPS information, and food-related information comprised in a photo content or input.

When a skin mode is selected on a gallery screen comprising the plurality of photo contents, the processor may be configured to filter only a skin-analyzed photo content, and to distinguishably display the filtered photo content with reference to the time at which the preset event related with skin care occurred.

The processor may be configured to add a graphic user interface (GUI) to the skin-analyzed photo content to distinguishably display the skin-analyzed photo content from the rest of the plurality of photo contents on the gallery screen.

When at least one face is detected from a preview screen provided for photographing, the processor may be configured to display at least one of a menu button regarding match or non-match with a previously registered user face, and a menu button regarding make-up or no make-up.

In one example embodiment, a method of controlling a display apparatus is provided, which may include receiving a command, and in response to receiving the command, distinguishably displaying a plurality of photo contents containing a user face based on a photographing time with reference to a time at which a preset event related with skin occurred.

When, based on a received command, a first photo content is selected among the photo contents photographed before the time at which the preset event occurred and a second photo content is selected among the photo contents photographed after the time at which the preset event occurred, the method may additionally include providing a user interface (UI) screen to compare skin conditions of the user face contained in each of the selected first and second photo contents.

The displaying may include displaying a graphic user interface (GUI) indicating the preset event between the photo contents photographed before and after the time at which the preset event occurred, such that the plurality of photo contents are distinguishably displayed with reference to the time at which the preset event occurred.

When the GUI is selected based on a received user command, the method may additionally include selecting a third photo content among the photo contents photographed before the time at which the preset event occurred, and selecting a fourth photo content having the photographing condition similar to that of the third photo content among the photo contents photographed after the time at which the preset event occurred, and providing UI screen to compare the skin conditions of the user faces respectively contained in the selected third and fourth photo content.

The photographing condition may include at least one of a face size, a face angle, a face expression, make-up or no make-up, presence or absence of accessory, and a photographing lighting.

Further, the preset event related with skin may include at least one of a skin care event, a skin treatment event, a product purchasing event related with skin, an event related with a change of location influencing the skin, an event related with weather influencing the skin, an event related with food consumption influencing the skin, and a holiday event.

Further, the method may include determining a preset event based on at least one of a skin-related event input on a preset calendar, a skin-related event included in a text message, GPS information, and food-related information included in the photo content or input.

Further, when skin mode is selected on gallery screen including a plurality of photo contents, the displaying may include filtering only the skin-analyzed photo content, and distinguishably displaying the photo content with reference to a time at which the preset event related with skin care occurred.

Further, the displaying may include adding GUI to the skin-analyzed photo content to identify the skin-analyzed photo content from the rest of the plurality of photo contents on the gallery screen and displaying the result.

Further, when at least one face is detected on the preview screen provided for photographing, the method may include displaying at least one of a menu button regarding match or non-match with a previously registered user face and a menu button regarding make-up or no make-up.

According to the above various example embodiments, the user convenience can be enhanced and an optimized UI screen for the skin-related services may be provided.

BRIEF DESCRIPTION OF THE DRAWINGS

The above and/or other aspects will be more apparent from the following detailed description, taken in conjunction with the accompanying drawings, in which like reference numerals refer to like elements, and wherein:

FIG. 2C is a diagram illustrating an example of various modules stored in a storage;

DETAILED DESCRIPTION

Figure 1A:
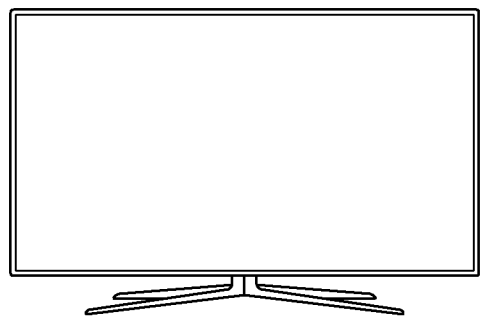
FIG. 1A is a diagram illustrating an example of a display apparatus according to an example embodiment.
Figure 1A:
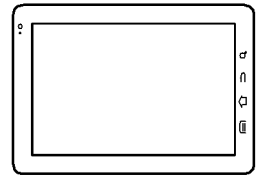
Figure 1A:
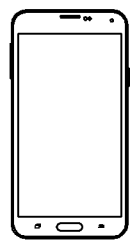
Figure 1A:
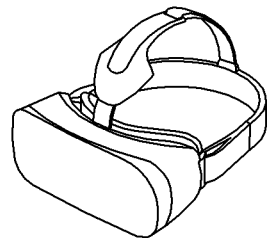

Certain example embodiments of the disclosure will now be described in greater detail with reference to the accompanying drawings.

In the following description, same drawing reference numerals are used for the same elements even in different drawings. The matters defined in the description, such as detailed construction and elements, are provided to assist in a comprehensive understanding of the disclosure. Accordingly, it is apparent that the example embodiments of the disclosure can be carried out without those specifically defined matters. Also, well-known functions or constructions may not be described in detail if they obscure the disclosure with unnecessary detail.

FIG. 1A is a diagram illustrating an example of a display apparatus according to an example embodiment.

As illustrated in FIG. 1A, the display apparatus 100 may take a form of a portable phone such as a smart phone, but is not so limited. Accordingly, various types of devices with a display function may be implemented, such as, tablet personal computer (PC), mobile phone, e-book, desktop personal computer (PC), laptop personal computer (PC), netbook computer, personal digital assistant (PDA), portable multimedia player (PMP), MP3 player, mobile medical device, camera, camcorder, electronic frame, wearable device (e.g., head mounted device (HMD), smart watch, electronic cloth, electronic bracelet, electronic necklace), near eye display (NED), large form display (LFD), digital signage, digital information display (DID), video wall, projector display, and so on. Further, the display apparatus 100 may include an embedded touch screen such that a program can be implemented with a finger or a pen (e.g., stylus pen).

The display apparatus 100 may provide skin analysis and skin care service regarding the user face included in photo content. For the above, the display apparatus may be implemented to store various programs for providing the skin analysis and the skin care service.

For example, the skin analysis and the skin care service according to an example embodiment may be provided in application form, which may, for example, be software directly used by a user on OS, and the application may be provided in the icon interface form on the display apparatus 100 screen. However, example embodiments are not limited thereto, and accordingly, the skin analysis and the skin care service may be provided in various forms according to implementation of the display apparatus 100.

Figure 1B:
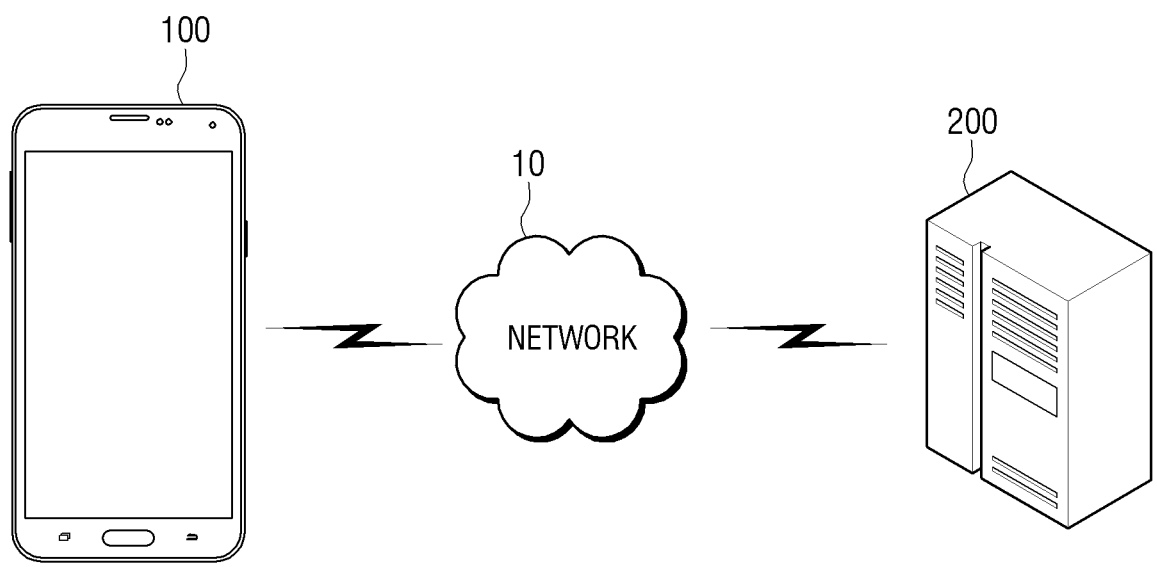
FIG. 1B is a diagram illustrating an example of a display apparatus according to another example embodiment.

FIG. 1B is a diagram illustrating an example of the display apparatus according to another example embodiment.

According to another example embodiment, the display apparatus 100 may be implemented to provide services by communicating with server 200 through a network 10. Herein, the display apparatus 100 may be implemented in the same form as the embodiment of FIG. 1A, which will not be further explained for the sake of brevity.

According to the example embodiment of FIG. 1B, the display apparatus 100 may provide UI screen for providing the skin analysis and the skin care service, and the photo content skin analysis may be performed through the server 200.

For example, when the photo contents for the skin analysis are transmitted to the server 200 from the display apparatus 100, the server 200 may perform the skin analysis regarding the user face area of the photo content, and provide the results to the display apparatus 100. Thereby, the server 200 may be implemented to perform the functions related with skin analysis explained in FIG. 1A.

The server 200 may be implemented, for example, to be a cloud server, although not limited thereto. "Cloud computing" may refer, for example, to cloud-based computing technology. For example, it may be web-based software service that keeps a program on the utility data server of the internet, calls and uses the program on a computer or a portable phone whenever such is necessary. When the server 200 is implemented to be a cloud server, the server 200 may be implemented to be a form that is capable of various product selling and ads service as well as simple information management. Further, the server 200 may be implemented to be embedded server provided within external server or the user terminal apparatus 100, according to the physical implementation form.

However, for the convenient explanation, various embodiments will be described in greater detail below based on the various embodiments illustrated in FIG. 1A.

Figure 2A:
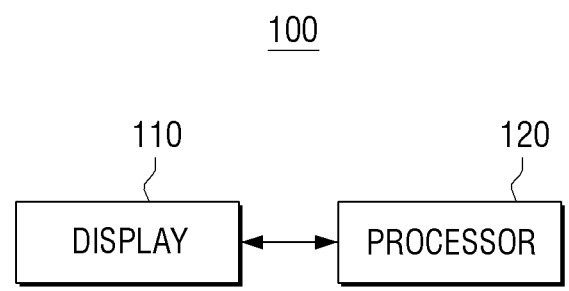
FIG. 2A is a block diagram illustrating an example display apparatus according to an example embodiment.

FIG. 2A is a block diagram illustrating an example display apparatus according to an example embodiment.

Referring to FIG. 2A, the display apparatus 100 may include a display 110 and a processor 120.

The display 110 may display various content such as still images, videos, texts, music, application implementing screen including various contents, graphic user interface (GUI) screen, and so on.

For example, the display 110 may display various UI screens for providing the skin analysis and the skin care service according to an example embodiment. Various examples of UI screens will be described below with reference to drawings.

Further, the display 110 may display an image, e.g., a preview image which is being photographed through camera module (not illustrated). According to examples, a specific area may be selected on the displayed image, in which case the display 110 may display expanded or detailed photographed image regarding the corresponding area. For example, the expanded image may be image of magnifying and then photographing the selected area, and the detailed photographed image may be image of focusing and magnifying and then photographing the corresponding area.

In this case, the display 110 may be implemented to be various forms of the display panels such as, for example, and without limitation, liquid crystal display (LCD), organic light-emitting diode (OLED), liquid crystal on silicon (LCoS), digital light processing (DLP) and quantum dot (QD) display panel, etc. For example, the display 110 may be implemented to be touch screen form which forms inter-layer structure with a touch pad. In this example, the display 110 may be used as user interface (not illustrated) which is described above as well as an outputting device. The touch screen may, for example, be configured to detect the touch input pressure in addition to the touch input position and dimensional area.

The processor 120 may control the overall operation of the display apparatus 100.

[Skin Analysis of User Face Included in Photo Content]

The processor 120 may provide various skin analysis services using, for example, previously installed applications.

The 'skin analysis service' may refer, for example, to a service to analyze the skin condition regarding the user face area from the photographed photo content and to provide the analyzed results.

For example, the display apparatus 100 may measure and analyze various skin conditions such as pore, acne, pigmentation, skin tone, dark circle, wrinkle, and so on from the user face. For the above, the processor 120 may be configured to perform a detailed photographing operation to focus, magnify and photograph the corresponding area in order to photograph one area of the user face in detail, according to various examples.

For example, the processor 120 may be configured to perform the identification regarding the face area included in the photographed image and perform the skin analysis regarding the recognized face area.

For example, the display apparatus 100 may perform the skin analysis regarding the corresponding face area when the photographed image is recognized as face of the previously registered user. In this example, the display apparatus 100 may perform the skin analysis only when the face area included in the photographed image meets certain example preset conditions, e.g., face size, face direction, or presence or absence of accessory (e.g., glasses). However, according to various examples, the skin analysis may be performed only regarding the image which is photographed under specific photographing conditions.

The processor 120 may be configured to analyze the skin of the user face area regarding at least one analyzing item when the user face is recognized. In this example, the processor 120 may perform the skin analysis only when the face included in the photographed image meets preset conditions. For example, the skin analysis may be performed only when the size of the face area is equal to, or greater than a preset size.

The analyzing items may include, for example, various items such as pigmentation, dot, freckle, skin tone, wrinkle, dark circle, and so on. In this example, the item to be analyzed may be an item set by default when the display apparatus 100 is manufactured or when the application is installed. However, according to various examples, the item to be analyzed may be item selected by a user from among the items that can be analyzed in the display apparatus 100.

Further, the processor 120 may be configured to perform the skin analysis only regarding the items that can be analyzed from the photographed image.

For example, when the area in the vicinity of the eyes is only confirmed from the photographed image, the display apparatus 100 may perform the skin analysis regarding the items that can be analyzed from the area in the vicinity to eyes, such as, wrinkle, dark circle, and so on. For another example, the display apparatus 100 only confirming the cheek area from the photographed image may perform the skin analysis only regarding the items that can be analyzed from the cheek area such as pigmentation, dot, freckle, skin tone, and so on.

The processor 120 may be configured to generate and provide UI screen to represent the skin analysis results regarding the user face area and show the analyzed results with various methods.

For example, the processor 120 may generate UI screen to distinguish each analyzing item with colors such that, for example, the acne is expressed in red, the pigmentation in blue, and so on, and then provide the same. Further, the processor 120 may generate UI screen to confirm the previous analyzed results, for example, express the improved area in green or blue and the deteriorated face area in red, and provide the same. According to various examples, when the area corresponding to specific face area or the area distinguished in color according to the analyzing item or analyzed result is selected from the photographed image, the processor 120 may provide the detailed analyzed image regarding the selected face area.

[Provision of UI Screen Based on Skin-Related Event]

The processor 120 may be configured to display a screen to distinguish and provide a plurality of photo contents including the user face with reference to the time at which the preset event related with skin has occurred.

In this example, the processor 120 may be configured to determine the points in time when each photo content is photographed based on the photographing time information tagged with each photo content. For example, the processor 120 may determine the time point when the photo content is photographed from exchangeable image file form (EXIF) information tagged with the photo content. Additionally, EXIF information may include information such as camera type, aperture number, shutter speed, exposure correction value, and so on.

The preset event related with skin may include at least one among a skin care event, skin treatment event, skin product purchasing event, event related with the change of location influencing the skin, event related with the weather influencing the skin, event related with the food consumption influencing the skin, and holiday event.

The skin care event may include, for example, the skin care event involving use of the dermatology or a skin care shop, the skin care event involving use of home care (massage care devices), and the skin care event involving use of a hot spring or spa. The skin treatment event may include the event of having the skin treatment such as razor treatment or medicine treatment at a dermatology clinic, a skin care shop or a private house.

The product purchasing event related with skin may, for example, be an event in which mask packs or cosmetics such as essence and cream are purchased. The change-of-location event influencing the skin may, for example, be an event of visiting a location showing different weather from that of the resident location (e.g., location influencing the skin such as foreign country having the high ultraviolet rays or foreign country having colder weather). The holiday event may include, for example, a case in which the holiday is spent in staying at home without the stress and abstaining from going out or a case in which a domestic travel or an overseas travel is made for the holiday. The weather change event influencing the skin may include event of rapid temperature drop or rise, snow or rain, and so on. Various other events that can influence the skin may be included.

The weather-related event influencing the skin may include, for example, various weather-related events that can influence the skin such as humidity, temperature, fine dust index, ultraviolet ray index, and so on.

The food consumption event influencing the skin may include, for example, various food consumption events which may, for example, be manually input by a user or recognized from the photographed picture, and can influence the skin. For example, it may be a case of consuming the food influencing the skin such as liquor, carbonated drink, greasy food, health food, and so on.

The processor 120 may be configured to determine whether the corresponding event has occurred based on at least one among the skin-related event input on a preset calendar, the skin-related event included in a text message, GPS information, and food-related information included in the photo content or input by a user.

For example, when a user drives a calendar application and inputs the skin-related event on the calendar screen (e.g., the dermatology, July $5^{th}$), the processor 120 may be configured to determine whether the corresponding event has occurred based on the inputs. Further, when a payment text message regarding the cosmetics being purchased is received, the processor 120 may recognize the receiving of the purchase and determine the occurrence of the corresponding event. For example, the message descriptions may be read using a related message reading technology such as optical message reader (OCR), magnetic message reader (MICR), and optical mark reading device (OMR), or the like.

The processor 120 may previously store various standard terms to determine the occurrence of the skin-related event. For example, various terms related with skin such as skin, dermatology, cosmetics, no make-up face, essence, mask pack, laser, care, care shop, lotion, cream, filler, and so on may be databased (DBed) and stored. Further, the processor 120 may database the skin-related terms input by a user. For example, when a user inputs the name of the dermatology clinic where a user is going to or the name of the cosmetics used by a user, the corresponding terms may be DBed.

The processor 120 may determine the corresponding event to be skin-related event when the corresponding terms are recognized from the schedule input on the calendar or the message descriptions (e.g., payment descriptions, reservation descriptions, progress inquiring descriptions (e.g., message descriptions asking the progress after the treatment from the dermatology)).

The processor 120 may determine the change-of-location event influencing the skin or the holiday event based, for example, on information in which the moving position of the display apparatus 100 is recorded and GPS information tagged with the photo content.

Further, the processor 120 may determine the weather change event influencing the skin based on the weather information obtained from a weather application or weather-related server.

When various skin-related events are determined, for example, as described above, the processor 120 may display the identification information indicating the corresponding events between the photo content photographed before and after the time at which the corresponding event is occurred, and thus distinguishably displays a plurality of photo contents based on the time at which the preset event occurred.

When skin mode is selected on gallery screen including a plurality of photo contents, the processor 120 may filter only the skin-analyzed photo content, and distinguishably display the photo content with reference to the time at which the preset event related with skin care occurred. In this example, the skin mode may be selected through a separate menu button, e.g., a menu button provided on the gallery screen.

In this example, the processor 120 may display the skin-analyzed photo content distinguishably from the other photo content among a plurality of displayed photo contents on the gallery screen. For example, the processor 120 may add the preset GUI to the skin-analyzed photo content and display the same. The GUI may include preset icons, preset symbols, preset boundaries, and so on.

However, example embodiments are not limited to the examples provided above. The processor 120 may display the skin-analyzed photo content distinguishably from the other content based on various methods such as differently displaying the frame of the photo content or differently displaying the brightness of the photo content, and so on.

The processor 120 may manage only the skin-analyzed photo content among a plurality of photo contents in a separate folder. Thus, a user may be provided with the gallery screen including only the skin-analyzed photo content by only selecting the corresponding folder without having to select the separate skin mode.

The processor 120 may filter and provide the photo content with various criteria based on receiving a command, such as, for example, a user command.

For example, when input with a user command such as command directing to view outdoor photos only, view indoor photos only, view only photo content in which the face size is equal to, or greater than a preset size, or view only photo content in which the face is in a forward direction, on UI screen that distinguishably provides the photo contents based on the skin-related event, the processor 120 may filter and provide the corresponding photo content. In this example, the processor 120 may filter the corresponding photo content through the photo image analysis, tagging EXIF information analysis, and so on.

[Provision of UI Screen for Comparing Skin Before and after Event]

When a first photo content is selected among the photo contents photographed before the time when the skin-related event occurred based on, for example, a user command, and when a second photo content is selected among the photo contents photographed after the time when the skin-related event occurred, the processor 120 may provide UI screen to compare the skin conditions of the user faces respectively included in the selected first and second photo content.

In response to selecting of GUI indicating the skin-related event based on a user command, the processor 120 may select a third photo content among the photo contents photographed before the time at which the corresponding event occurred (e.g., most recently photographed photo among the photo contents photographed before the time when the corresponding event occurred or photo in which the photographing condition is most proper to the preset condition among the recently photographed photos). The processor 120 may select a fourth photo content in which the photographing condition is similar to that of the third photo content among the photo contents photographed after the time when the corresponding event occurred, and provide UI screen to compare the skin conditions of the user faces respectively included in the selected third and fourth photo content. The photographing conditions may include at least one among the user face size, the user face angle, with or without make-up, presence or absence of accessory, and the photographing lighting.

In this example, the processor 120 may adjust the arrangement positions and sizes of the photo content photographed before and after the corresponding event to suit various environments, and provide the same.

For example, the processor 120 may determine the arrangement positions of the photo content photographed before and after the corresponding event based on the arrangement mode of the display apparatus 100.

For example, the processor 120 may provide the photo content photographed before the corresponding event on the left side of the screen and the photo content photographed after the corresponding event on the right side of the screen, when, for example, the display apparatus 100 is in horizontal mode. Further, the processor 120 may provide the photo content photographed before the corresponding event on the upper side of the screen and the photo content photographed after the corresponding event on the lower of the screen, when the display apparatus 100 is in vertical mode.

For another example, the processor 120 may provide the photo content photographed before the corresponding event and the photo content photographed after the corresponding event in the same size for the convenient comparison, but is not limited to the above. According to various examples, the processor 120 may provide the photo content photographed before the corresponding event in a smaller size than the photo content photographed after the corresponding event.

The processor 120 may provide the skin comparison UI screen in different forms based on the arrangement mode of the display apparatus 100. For example, the processor 120 may provide UI screen to compare the photo content photographed before the corresponding event with the photo content photographed after the corresponding event. Further, it may provide the skin comparison results in the text form or provide the skin care recommend information based on the skin comparison results when the display apparatus 100 is changed into the vertical mode.

The processor 120 may adjust the size of each photo content based on a received command, such as, for example, a user command (e.g., touch interaction). In this example, the processor 120 may provide the skin analysis information in different forms based on the sizes of the photo content. For example, the processor 120 may provide the analysis information in the image form when the photo content is equal to, or greater than a preset size, and provide the analysis information in the text form when the photo content is less than a preset size. For example, the processor 120 may highlight and provide the pigmentation area near to the cheek with a specific color, or provide the text form such as "increase in the pigmentation of the left cheek" or "surrounding area of the left cheek: two pigmentation spots".

[Provision of UI Screen Related with Photographing]

The processor 120 may provide various menus to provide the skin analysis and the skin care service according to an example embodiment on the photographing complete screen and the preview screen for the photographing.

When a photo including the human face satisfying a preset condition is photographed while the user face is not registered, the processor 120 may provide UI menu to confirm whether or not the human face is user face immediately after the photographing is completed. For example, while asking whether or not the photographed face is user face, it may provide a notification that the skin changes will be compared and managed based on the photographed face. Thereafter, the processor 120 may register the user face when such is confirmed, and store the user face as a subject image for the skin analysis/change management.

When at least one face is detected from the preview image for the photographing in a state that the user face is registered, the processor 120 may display on the preview screen at least one of a menu button as to matching the previously registered user face or not, and a menu button as to presence or absence of make-up.

For example, when one face is detected from the preview image and the detected face is determined to match a registered user face, the processor 120 may provide GUI button to select whether the face is with or without make-up on the screen. The photographing may be performed after a user selecting is completed. In this example, a photo may be stored when the corresponding GUI button is selected and then a shutter button is selected. Alternatively, a screen may be provided with the shutter button being automatically selected, in which case photographing can be performed automatically, i.e., by only requiring the operation of a corresponding GUI button.

As another example, when one face is detected from the preview image and when the detected face does not match the registered user face, the processor 120 may provide GUI button to confirm a user as well as GUI button to select whether the face is with or without make-up. In this example, the photographing may be performed only after confirming the user, followed by confirming whether the face is with or without make-up. Again, a screen may be provided with the shutter button being automatically selected, in which case the photographing may be automatically performed only by requiring consecutive operation of the corresponding GUI buttons.

As another example, when a plurality of faces are detected from the preview image, the processor 120 may display GUI to recognize the face that matches the registered user face, and provide GUI buttons to select whether the face is with or without make-up near to the recognized face. In this example, the processor 120 may perform the skin analysis only regarding the face that matches the registered user face among a plurality of detected faces.

Further, when there is no face that matches the registered user face among a plurality of detected faces, the processor 120 may display GUI to select the face for the skin analysis and perform the skin analysis regarding the selected face.

[Implementation of Service]

The service according to the above example embodiment may be a service form provided by interoperating functions of the related applications. However, it may take a service form provided from new application.

For example, the related gallery application may be interoperated with the calendar application, and the skin-related schedule input through the calendar application may be applied to the gallery application. However, when a text message reading function (or mail reading function) is used, a text message application (or mail application) may be additionally interoperated. Further, when a camera photographing function is used, the camera application may be additionally interoperated.

As another example, all the services according to an example embodiment may be implemented to be separate new applications, e.g., skin care applications, which provide UI screen to provide the gallery function within the corresponding application, UI screen to provide the calendar function, and the camera photographing function. In this example, because all the schedules input through UI screen to provide the calendar function are determined as schedule related with skin. Thus, another determination regarding the schedule may not be necessary. Also, only some functions may be implemented in the corresponding application and the other functions may be used by interoperating a related application.

Figure 2B:
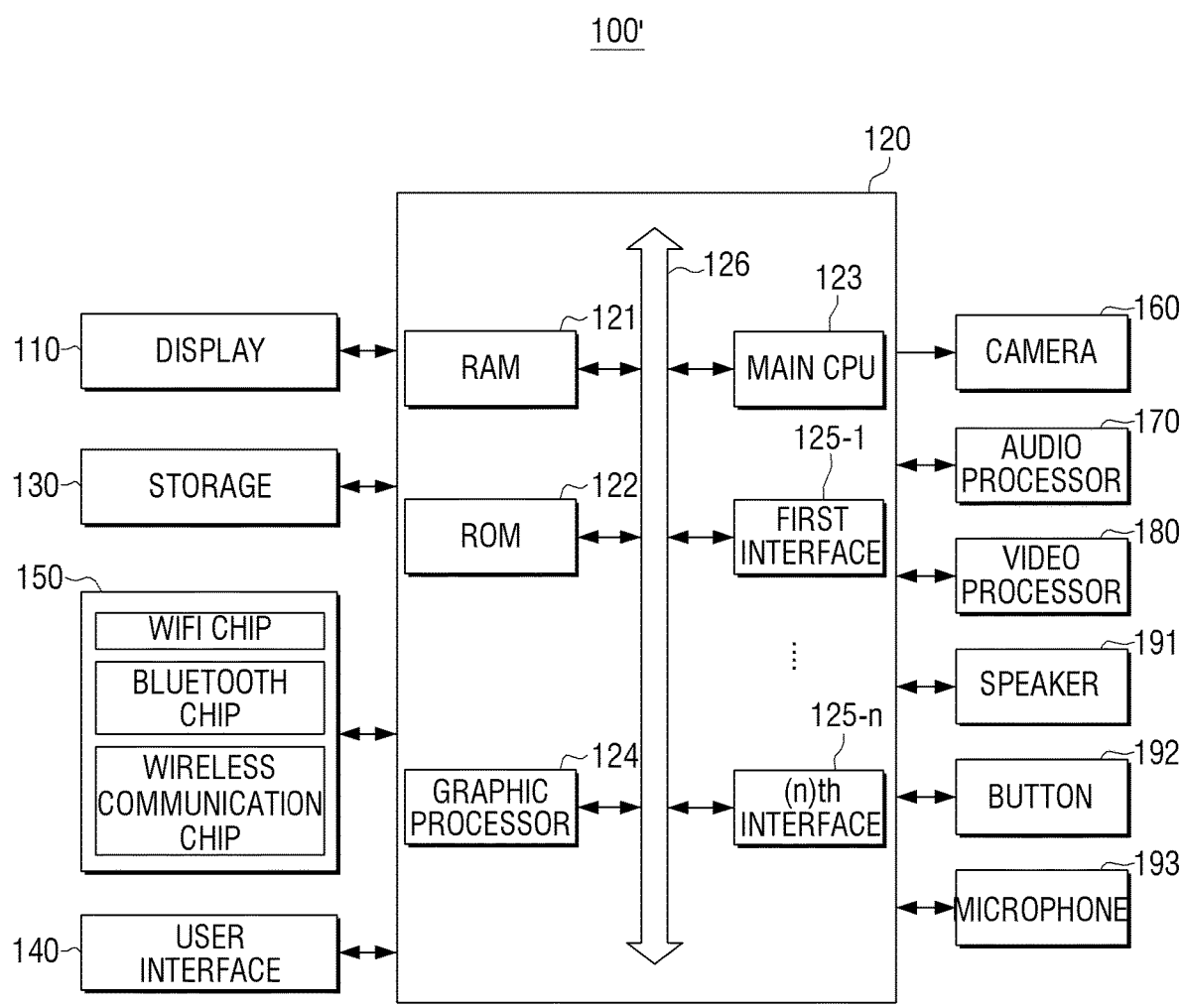
FIG. 2B is a block diagram illustrating an example of the display apparatus of FIG. 2A.

FIG. 2B is a block diagram illustrating an example of the display apparatus illustrated in FIG. 2A.

Referring to FIG. 2B, the display apparatus 100' may include the display 110, the processor 120, a storage 130, a user interface 140, a communicator (e.g., including communication circuitry) 150 and the camera 160. Further explanation will not be provided herein regarding the elements illustrated in FIG. 2B that are overlapped with the elements illustrated in FIG. 2A.

The processor 120 may include, for example, RAM 121, ROM 122, a main CPU 123, a graphic processor 124, first to (n)th interfaces 125-1 to 125-*n*, and a bus 126.

RAM 121, ROM 122, the main CPU 123, the graphic processor 124, and the first to (n)th interface 125-1 to 125-*n* may be connected to each other through the bus 126.

The first to (n)th interface 125-1 to 125-*n* may be connected to the elements described above. One of the interfaces may be network interface connected to an external device through the network.

The main CPU 123 may access the storage 130, and perform the booting by using the stored O/S in the storage 130. Further, the main CPU may perform various operations by using the various programs, content and data stored in the storage 130.

ROM 122 may store command sets for the system booting. When a turn-on command is inputted and the electrical power is provided, the main CPU 123 may copy the stored O/S in the storage 140 to RAM 121 according to the stored commands in ROM 122, and boot the system by implementing O/S. When the booting is completed, the main CPU 123 may copy the various programs stored in the storage 130 to RAM 121, and perform various operations by implementing the programs copied to RAM 121.

The graphic processor 124 may generate the screen including various objects such as icons, images, and texts by using a calculator (not illustrated) and a renderer (not illustrated). The calculator (not illustrated) may calculate feature values such as coordinate values, shapes, sizes and colors in which each object will be displayed according to the layout of the screen based on the received control command. The renderer (not illustrated) may generate various layouts of the screen including objects based on the calculated feature values in the calculator (not illustrated).

Meanwhile, the above described operation of the processor 120 may be performed by the programs stored in the storage 130.

The storage 130 may store various data such as O/S (Operating System) software module to drive the display apparatus 100' and various multimedia contents. The following will explain more detailed operation of the processor 120 to use the programs stored in the storage 130.

FIG. 2C is a diagram illustrating various example modules that may be stored in the storage.

Referring to FIG. 2C, the storage 130 may store software including base module 131, sensing module 132, communication module 133, presentation module 134, web browser module 135, service module 136, image analyzing module 137, and skin analysis module 138.

The 'base module 131' refers to a basic module to process the signals delivered from each hardware included in the display apparatus 100' and deliver the processed signals to upper layer module. The base module 131 may include storage module 131-1, security module 131-2, and network module 131-3. The storage module 131-1 is program module to manage database or registry. The main CPU 123 may access the database within the storage 130 by using the storage module 131-1, and read various data. The security module 131-2 may be program module to support hardware certification, request permission, and secure storage. The network module 131-3 may be module to support the network connection, and include DNET module and UPnP module.

The sensing module 132 may be a module to collect information from various sensors, analyze and manage the collected information. The sensing module 132 may include head direction recognizing module, face recognizing module, voice recognizing module, motion recognizing module, touch recognizing module, gesture recognizing module and NFC recognizing module.

The communication module 133 may be provided to perform the communication externally. The communication module 133 may include messaging module 133-1 such as messenger program, short message service (SMS) & multimedia message service (MMS) program, and e-mail program and call module 133-2 including call info aggregator program module and VoIP module.

The presentation module 134 may be a module to create the display screen. The presentation module 134 may include multimedia module 134-1 to reproduce and output multimedia content, and UI rendering module 134-2 to perform UI and graphic processing. The multimedia module 134-1 may include player module, camcorder module and sound processing module. Thereby, the multimedia module 134-1 may perform the operation to generate and reproduce the screen and the sound by reproducing various multimedia content. UI rendering module 134-2 may include image compositor module to combine images, coordinate combine module to combine coordinates on the screen where an image will be displayed, X11 module to receive various events from the hardware, and 2D/3D UI toolkit to provide tools for constituting UI in 2D or 3D form.

The web browser module 135 refers to module to access the web server by performing the web browsing. The web browser module 135 may include various modules such as web view module to constitute web pages, download agent module to perform the downloading, bookmark module, and webkit module.

The service module 136 may be a module including various applications to provide various services. For example, the service module 136 may include various programs such as SNS program, content reproducing program, game program, electronic book program, calendar program, alarm management program, and other widgets.

The image analyzing module 137 may be provided to recognize the user face by analyzing the photographed images. In this example, the image analyzing module 137 may store face recognition algorithms. For example, the image analyzing module 137 may recognize the eye area from the photographed image through the face modeling technology by using the face recognition algorithms. Herein, the 'face modeling technology' may refer, for example, to analyzing process to process the face image included in the photographed image and convert into the digital information for the transmission; one of active shape modeling (ASM) technology and active appearance modeling (AAM) technology may be used.

The skin analysis module 138 may be provided to analyze the skin of the user face area regarding at least one analyzing item. Herein, the analyzing item may include various items such as pigmentation, dot, freckle, skin tone, wrinkle, dark circle, and so on. In this case, the skin analysis module 138 may store information regarding the item to be analyzed and analyzing algorithms per item.

Although FIG. 2C illustrates various program modules, the illustrated various program modules may be partly removed and modified, or new program module may be added based on the type and the feature of the display apparatus 100'. For example, it may be implemented to further include position base module to support position base service by interoperating with the hardware such as GPS chip.

Further, the storage 130 may store the skin analysis information and the user identification information.

The skin analysis information may include, for example, analysis of the skin of the user face area based on the above described various analyzing items. For example, the skin analysis information may include information of analyzing whether specific face area includes the pigmentation, the skin tone, the dot, or the acne, information regarding previous analysis according to the respective items, and history information representing the skin analysis results regarding each face area according to the time order.

The user recognition information may be information of recognizing the specific user face. Thereby, the user recognition information may include a general face image of a user, and images regarding the face parts included in the face area (e.g., eye, nose, lip). For example, the processor 120 may recognize a user using the user recognition information and comparing the recognized eye area from the photographed image with the previously stored user eye area.

The user interface 140 may receive various user commands.

For example, the user interface 140 may be implemented using various interface circuitry, including, for example, the touch pad or the touch screen, and to receive user touch interaction for controlling the user terminal apparatus 100.

For example, the user interface 140 may receive user interaction regarding various UI screen provided through the touch screen. The UI screen may be various UI screens for providing the skin analysis and the skin care service according to an embodiment. In this example, UI screen may be implemented in various forms such as various content reproducing screen like images, videos, texts, and music, application implementing screen including various content, web browser screen, and graphic user interface (GUI) screen.

The communicator 150 may perform the communication with an external device (not illustrated). Herein, the communicator 150 may perform the communication with an external device (not illustrated) through various communication circuitry and methods such as, for example, and without limitation, Bluetooth (BT), Wireless Fidelity (WI-FI), Zigbee, Infrared (IR), Serial Interface, Universal Serial Bus (USB), Near Field Communication (NFC), and so on.

The external device (not illustrated) may include various external servers as well as various electronic devices.

For example, when the preset event has occurred, the communicator 150 may operate in the interoperating state by performing communication with the external device (not illustrated) based on the previously defined communication method. Herein, the 'interoperating' may refer, for example, to any state in which the communication is available, such as, operation to initialize the communication between the display apparatus 100' and the external device (not illustrated), operation to form the network, operation to perform the device pairing, and so on. For example, the device identification information of the display apparatus 100' may be provided to the external device (not illustrated) and the pairing process between the two devices may be performed. For example, when the preset event (e.g., device selecting command, device turn-on command) has occurred in the user terminal apparatus 100, the communicator 150 may search surrounding devices through digital living network alliance (DLNA) technology, and may operate in the interoperating state by performing the pairing with the searched device.

For example, the communicator 150 may transmit the photo content for the skin analysis to the server 200 when the external server 200 performs the skin analysis according to the example embodiment of FIG. 1B, and receive the results in which the skin analysis is performed regarding the user face of the photo content.

The camera 160 may photograph an object according to a user command.

When the object is photographed through the camera 160, the object may be converted into the electrical image signals through charge coupled device (CCD), and the converted image signals may be converted into the amplified and digital signals in an analogue signal processor (not illustrated). The digital signals converted as described above may be digitized at a digital signal processor (not illustrated), and expressed through the display 110 after being adjusted with the color and the brightness under the controlling of the processor 120. According to various examples, the camera 160 may put the focus on the user face area, magnify and photograph with the controlling of the processor 120.

According to various example embodiments, the processor 120 may determine the lighting environment of the photographed image, using an auto white balance setting function. For example, the processor 120 may photograph an image such that the uniform white balance can be set by using the calculated lighting environment. Further, the processor 120 may adjust the light source (e.g., LED light source) included within the display apparatus 100' under the photographing environment in which there is no external light and photograph an image such that the uniform white balance can be set.

When the photographing is performed by setting the white balance according to the auto white balance setting function, the processor 120 may set the face area of the photographed image in different colors according to the set white balance in response to each photographed image, and then photograph the same.

In order to uniformly set the color feeling of the face area regarding various images, the processor 120 may shield the external light source, and use only the light source included in the display apparatus 100'.

Further, according to various example embodiments, the display apparatus 100' may include a front face camera or a back face camera. For example, when an image is photographed by using the front face camera, the back face camera may determine the photographing environment and set the white balance of an image to be photographed such that an image can be photographed under the uniform photographing environment.

An audio processor 170 is provided to process the audio data. The audio processor 170 may perform various processes such as decoding, amplifying, and noise filtering of the audio data.

A video processor 180 is provided to process the video data. The video processor 180 may perform various image processes such as decoding, scaling, noise filtering, frame rate converting, and resolution converting regarding the video data.

A speaker 191 is provided to output various alarm sounds and voice messages as well as audio data processed in the audio processor 170.

A button 192 may be various types of button such as mechanical button formed on any area such as front area, side area, and back area of the exterior main body of the display apparatus 100', touch pad, wheel, and so on. For example, a button to turn on/off the electrical source of the display apparatus 100' may be provided.

A microphone 193 is provided to receive user voices or other sounds and convert into the audio data. The processor 120 may use the user voices inputted through the microphone 193 during a call, or convert into the audio data and store in the storage 130. Meanwhile, the camera 160 and the microphone 193 may be a part of the user interface 140 described above, depending on functions thereof.

When the camera 160 and the microphone 193 are provided, the processor 120 may perform the control operation according to the user voice input through the microphone 193 or the user motion recognized by the camera 160. Thus, the display apparatus 100' may operate in a motion control mode or a voice control mode. When operating in the motion control mode, the processor 120 may photograph a user by activating the camera 160, and perform the corresponding control operation by following the changes in the user motion. When operating in the voice control mode, the processor 120 may operate in a voice recognizing mode to analyze the user voices inputted through the microphone and perform the control operation according to the analyzed user voices.

Meanwhile, although not illustrated, the display apparatus 100' may further include a feedback provider (not illustrated) and GPS receiver (not illustrated). The feedback provider (not illustrated) may perform a function to provide various feedbacks (e.g., audio feedbacks, graphic feedbacks, haptic feedbacks) according to the displayed UI screen. For example, while the skin analysis is being performed, when the skin-related event has occurred, or when UI screen for the skin comparing is provided, the feedback provider (not illustrated) may provide the corresponding feedback. GPS receiver (not illustrated) may receive GPS signals from Global Positioning System (GPS) satellite and calculate the current position of the display apparatus 100' or perform a function to tag the photographed photo content with the current position.

FIG. 2B illustrates an example embodiment of the detailed elements included in the display apparatus 100'. According to an example embodiment, some elements illustrated in FIG. 2B may be partly removed or modified, and other new elements may be added.

Figure 3A:
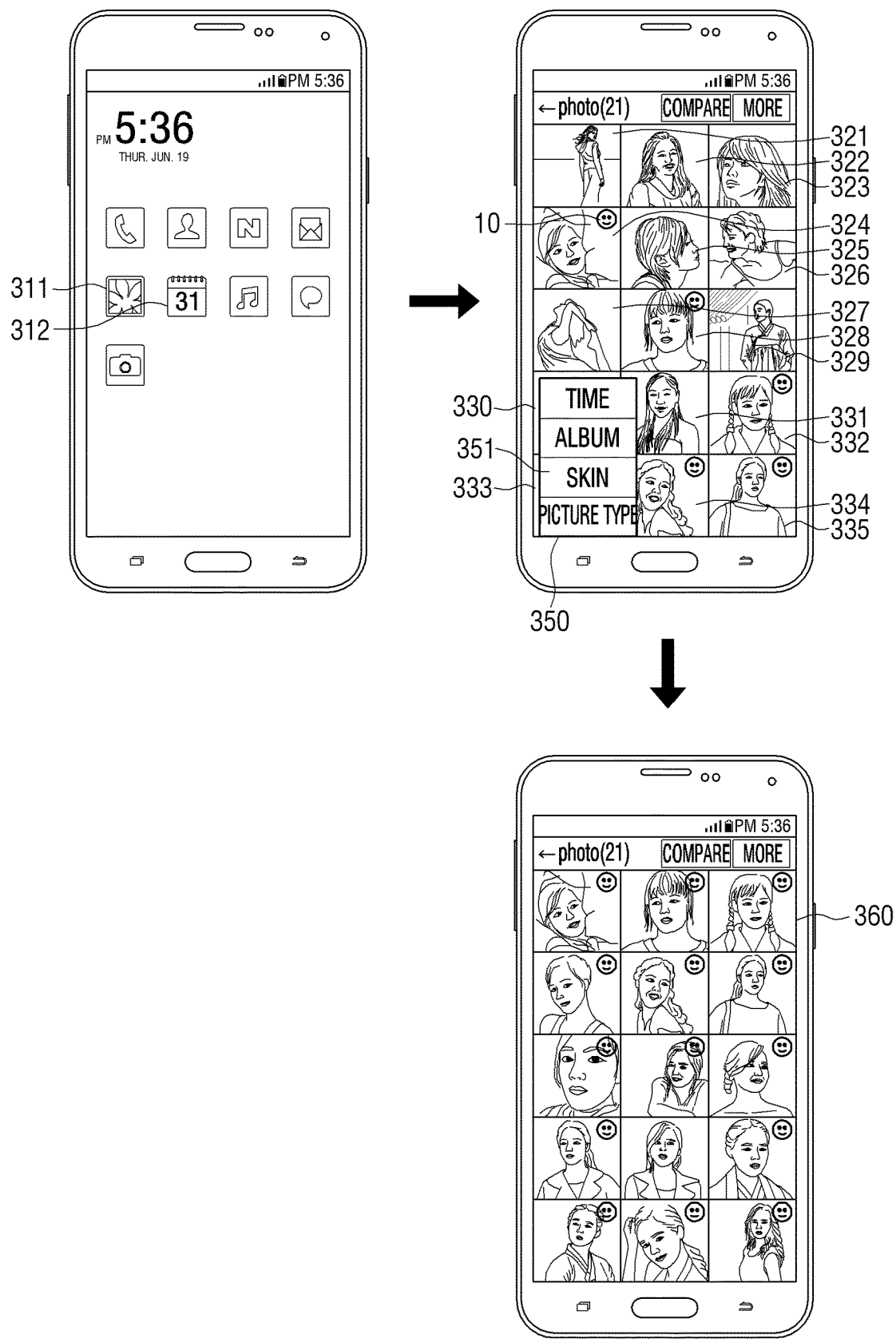
FIGS. 3A and 3B are diagrams illustrating an example of a service according to various example embodiments.
Figure 3B:
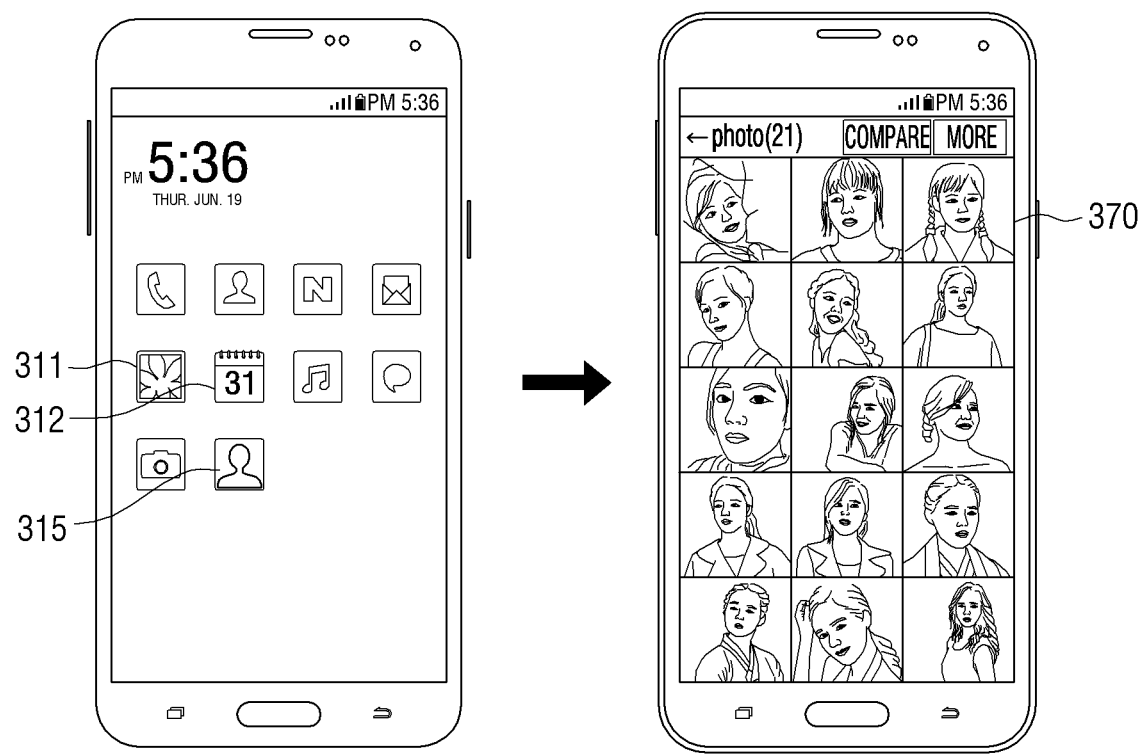

FIGS. 3A and 3B are diagrams illustrating an example of the service according to various example embodiments.

FIG. 3A illustrates an example of the service according to an example embodiment. When a user selects and drives the gallery application 311 on the illustrated UI screen, the gallery screen including a plurality of photo contents 321 to 335 may be provided. In this example, GUI 10 to distinguish the photo contents 324, 328, 332, 334, 335 in which the skin analysis is performed from the other photo contents may be provided. When a user selects a skin item 351 from the provided menu 350, the gallery screen 360 including only the skin-analyzed photo content may be provided.

FIG. 3B illustrates an example of the service according to an example embodiment. When a user selects and drives the skin service application 315 as illustrated, the gallery screen 370 including only the skin-analyzed photo content may be immediately provided. The skin service application 315 may, for example, be application separately manufactured to provide the skin-related service according to the invention. For example, the skin service application 315 may be implemented to provide various functions such as photographing function, calendar function, and skin analysis function to provide the skin-related services according to an example embodiment.

Figure 4A:
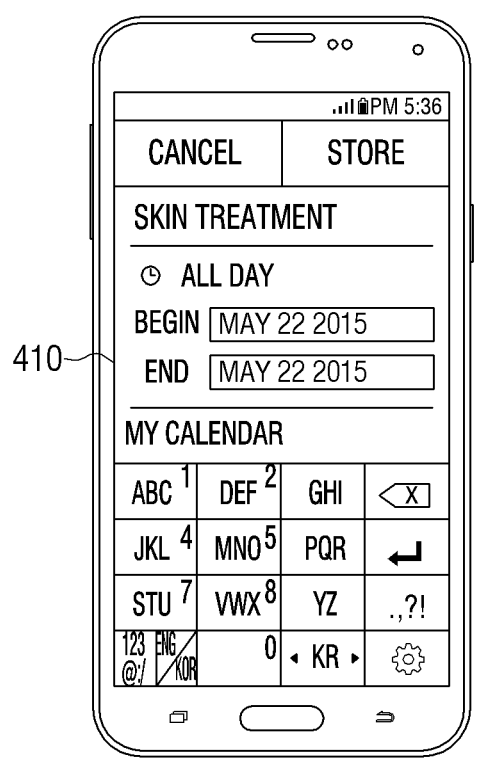
FIGS. 4A and 4B are diagrams illustrating an example method for inputting skin-related schedules on a calendar according to an example embodiment.
Figure 4B:
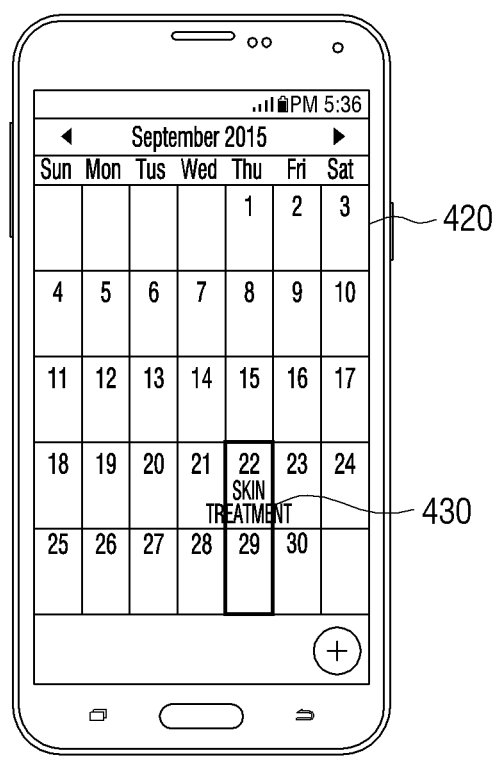

FIGS. 4A and 4B are diagrams illustrating an example method for inputting the skin-related schedule on the calendar according to an example embodiment.

When a user drives the calendar (or planner) application 312 on UI screen illustrated in FIG. 3A and inputs the skin-related schedule through UI screen 410 for inputting the schedule as illustrated in FIG. 4A, the skin-related schedule 430 may be input to the calendar 420, as illustrated in FIG. 4B.

In this example, the processor 120 may extract the skin-related schedule among the various schedules input to the calendar 420 and use the extracted schedule in providing various services according to an example embodiment, which will be explained in greater detail below.

Example embodiments may not be limited to the examples provided above. Accordingly, UI screen 410 for inputting the schedule illustrated in FIG. 4A may be provided as UI screen of the skin service application 315 illustrated in FIG. 3B. In this example, the processor 120 may determine all the input schedules as skin-related schedules. For example, even when the schedule does not include DB terms related with skin, the processor 120 may determine the schedule as skin-related schedule.

Figure 5A:
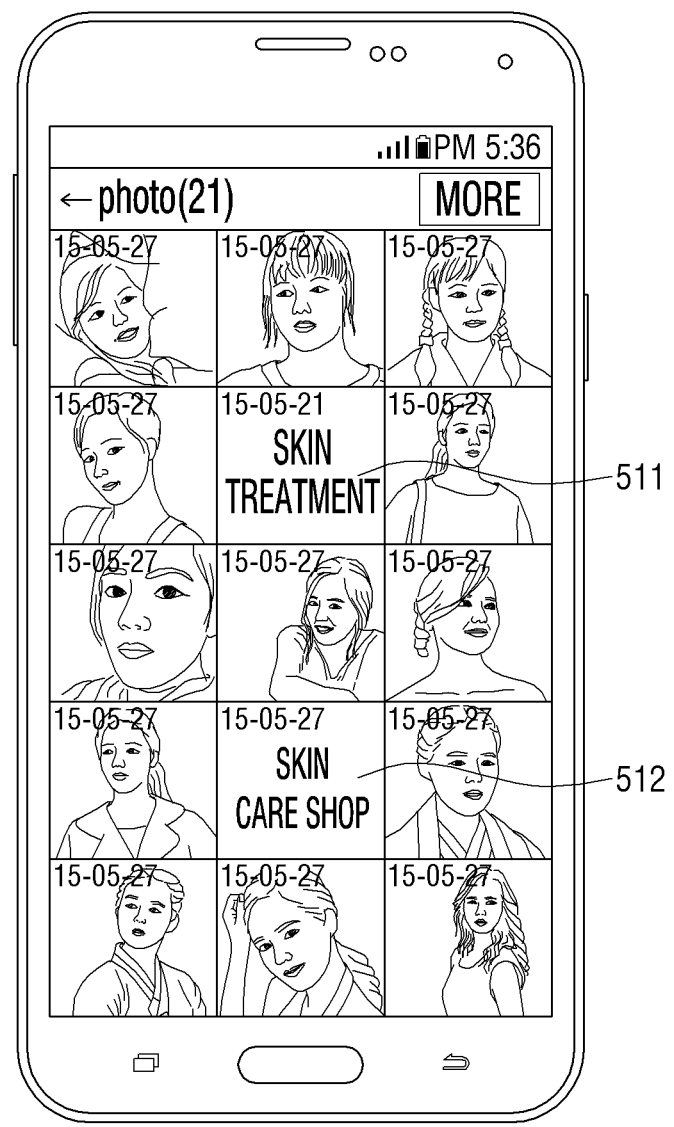
FIGS. 5A and 5B are diagrams illustrating example UI screens according to an example embodiment.
Figure 5B:
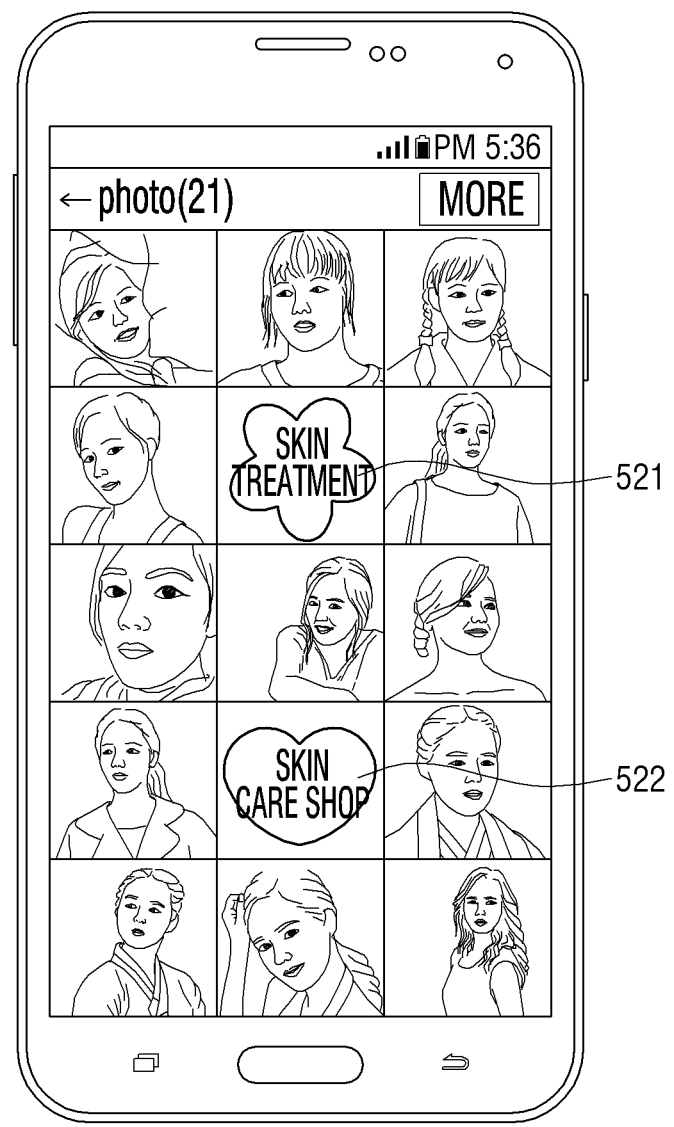

FIGS. 5A and 5B are diagrams illustrating an example UI screen according to an example embodiment.

According to an example embodiment, the processor 120 may distinguishably display a plurality of photo contents with reference to the time at which the preset event related with skin has occurred based on the photographing time of a plurality of photo contents.

For example, the skin-analyzed photo content as illustrated in FIG. 5A may be distinguished and provided based on the criteria of the skin-related schedule input in FIG. 4B, e.g., the schedules of "May 21$^{st}$, skin treatment" 511 and "May 27$^{th}$, skin care shop" 512.

For example, the skin-related event may be provided in GUI having the same form and size as the photo content, although not limited thereto. For example, as illustrated in FIG. 5B, the skin-related event may be provided in a preset form of the icons 521, 522. These icons may be stored as default, although a user may directly produce the icons, or select and use the icons from the preset icons.

As illustrated in FIG. 5A, the weather and the time (or date) in which the corresponding photo content is photographed may be marked on the photo content. However, as illustrated in FIG. 5B, the weather and the time may be displayed only when a user selects.

According to the above described example embodiments, a user may distinguish the photo content photographed before and after the time of the skin-related event with one quick view, and easily observe the skin changes before and after the corresponding event.

Figure 6:
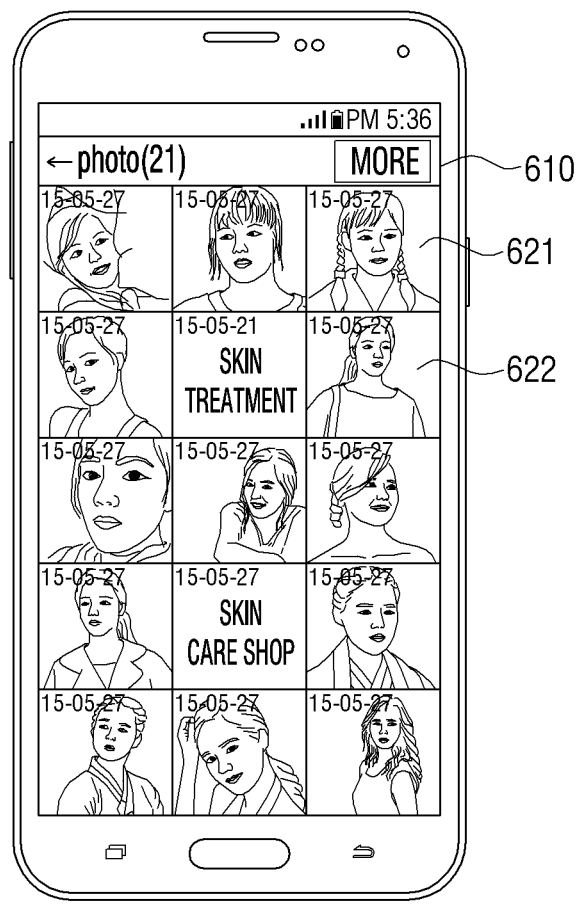
FIG. 6 is a diagram illustrating an example UI screen according to another example embodiment.
Figure 6:
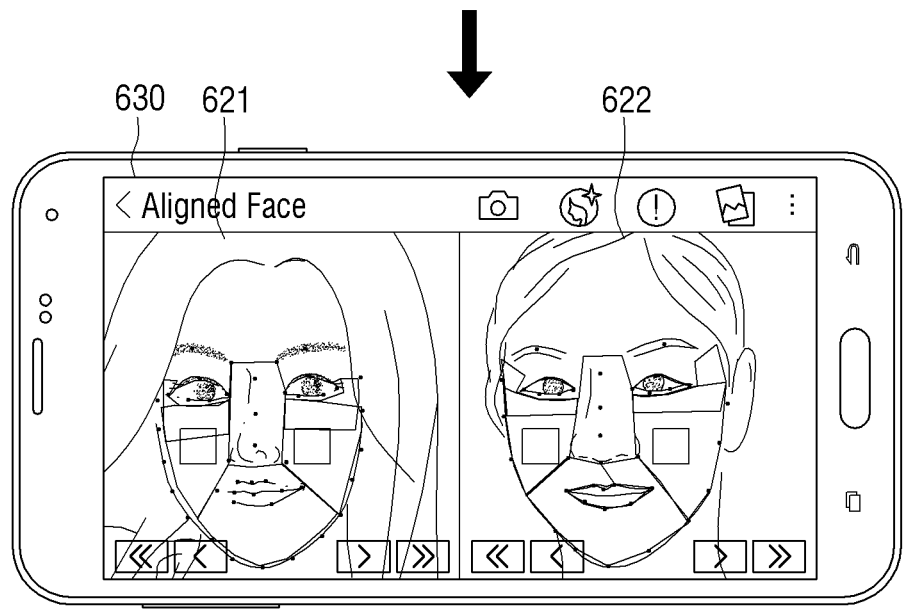

FIG. 6 is a diagram illustrating an example UI screen according to another example embodiment.

As illustrated in FIG. 6, when a user selects the photo content 621, 622 before and after the specific skin-related event on UI screen 610 including the skin-analyzed photo content, UI screen 630 to compare the skin conditions of the user faces included in the selected photo content 621, 622 may be provided.

The corresponding UI screen 630 may be provided with the screen in which the skin conditions of the user faces included in the selected photo content 621, 622 are specifically compared and analyzed with each other.

The photo content 621 photographed before the skin-related event may be provided on the left side of the screen, and the photo content 622 photographed after the skin-related event may be provided on the right side of the screen, although not specifically limited thereto. For example, when the screen is in vertical mode, the photo content 621 photographed before the skin-related event may be provided on the upper side of the screen, and the photo content 622 photographed after the skin-related event may be provided on the lower side of the screen.

Further, the photo content 621 photographed before the skin-related event and the photo content 622 photographed after the skin-related event may be provided in the same size as illustrated for the convenient comparison, although not limited thereto. For example, the photo content 621 photographed before the skin-related event may be provided in a smaller size than that of the photo content 622 photographed after the skin-related event.

Figure 7A:
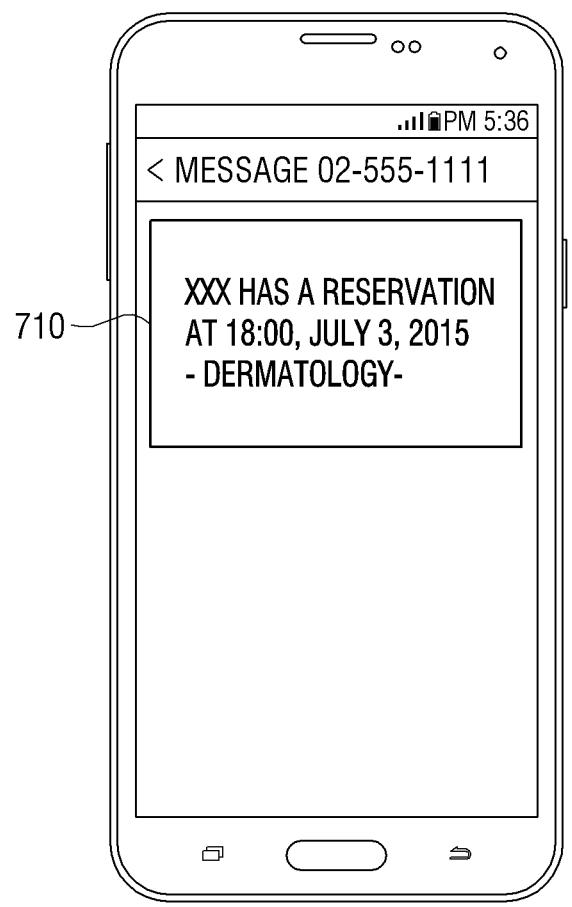
FIGS. 7A to 7C are diagrams illustrating an example method for extracting a skin-related event from a message according to another example embodiment.
Figure 7B:
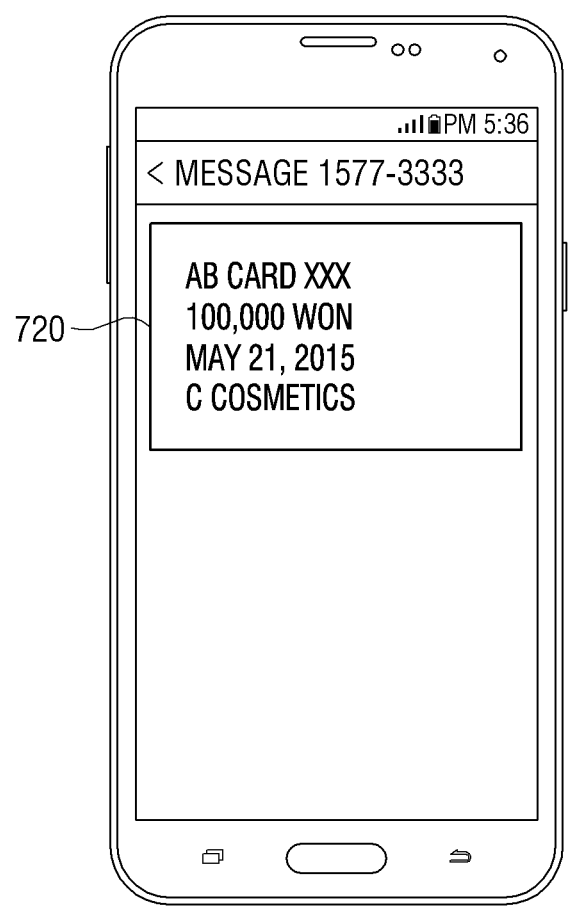
Figure 7C:
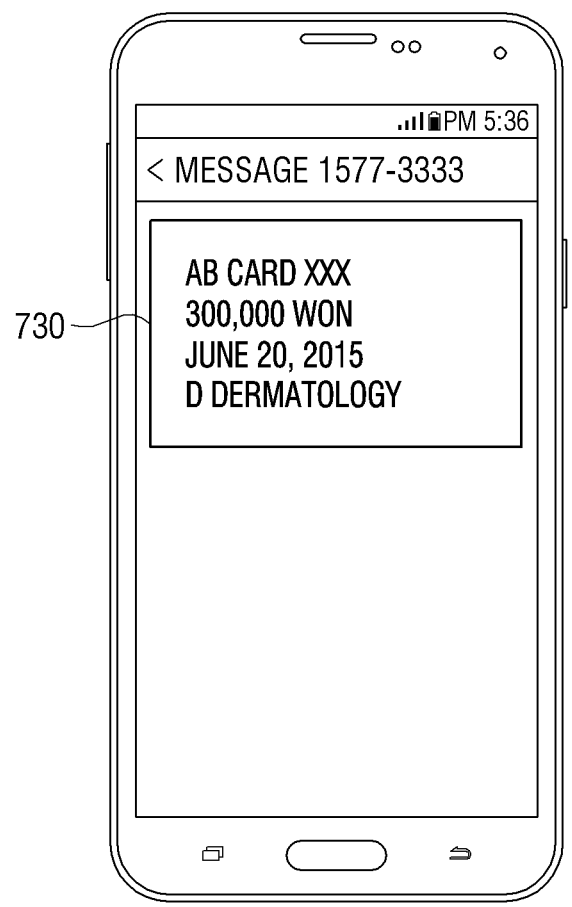

FIGS. 7A to 7C are diagrams illustrating an example method for extracting the skin-related event on a message according to another example embodiment.

As illustrated in FIGS. 7A to 7C, when a skin-related text message is received, the processor 120 may recognize the message and determine whether the skin-related event is occurred. For example, the processor 120 may determine the skin-related events such as "dermatology reservation (FIG. 7A)" 710, "cosmetics purchasing (FIG. 7B)" 720 and "dermatology payment (FIG. 7C)" 730 from the text message descriptions by using OCR, MICR, and OMR technology.

For example, the processor 120 may determine whether the received text message descriptions 710, 720, 730 correspond to the skin-related events based on DB standard terms. For example, when the text message includes the standard terms such as "dermatology" and "cosmetics," the text message may correspond to the skin-related event.

According to various examples, when the skin-related event is extracted from the received text message descriptions, the processor 120 may provide a notice window to a user, asking whether the corresponding event is added as skin-related event. In this example, the processor 120 may add the corresponding event as skin-related event only when a user approves the adding of the corresponding event as skin-related event, and may ignore the corresponding event when a user does not approve.

Figure 8:
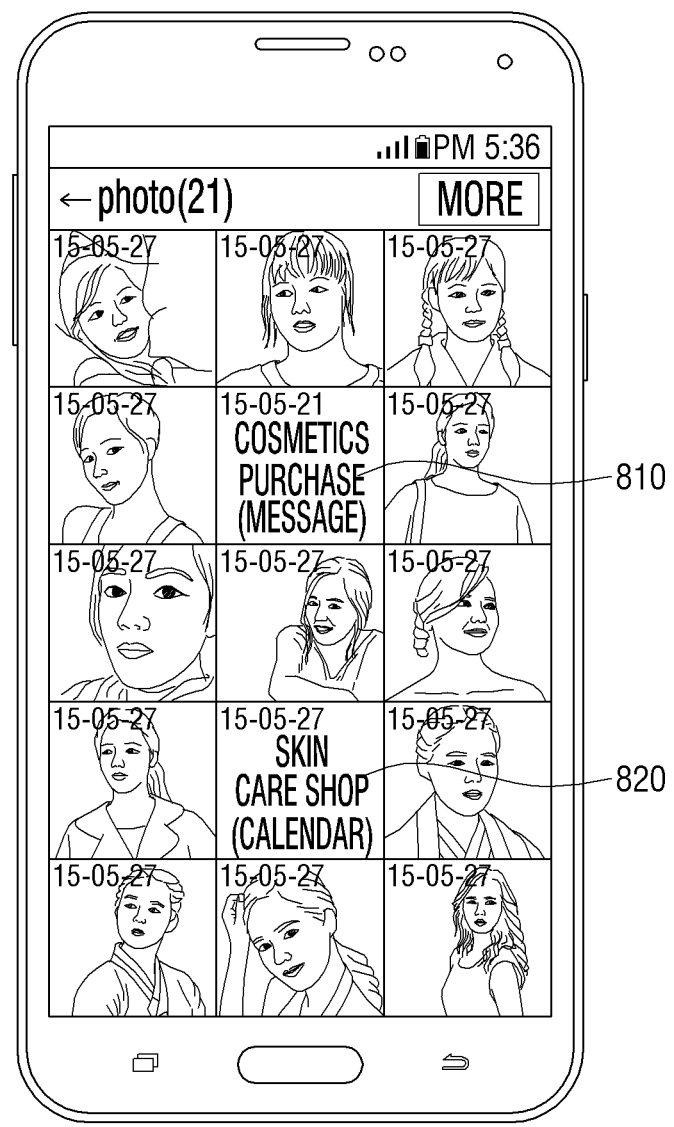
FIG. 8 is a diagram illustrating an example UI screen according to another example embodiment.

FIG. 8 is a diagram illustrating an example UI screen according to another example embodiment.

According to another example embodiment, the skin-related event extracted through the text message descriptions illustrated in FIGS. 7A to 7C may be applied as the criteria to distinguish the photo content automatically or based on a user selection, as illustrated in FIG. 8.

For example, the cosmetics purchasing event of May 21, 2015 which is generated through the text message descriptions illustrated in FIG. 7B may be used as skin-related event 810 to distinguish the photo content, as illustrated.

In this example, GUI 810, 820 respectively indicating the events may be provided with the identification information (e.g., message, calendar) indicating the applications in which the events are respectively generated, as illustrated. However, this is merely one of various example embodiments. According to another example embodiment, only the event title may be displayed without the information regarding the applications in which the events are generated.

Figure 9:
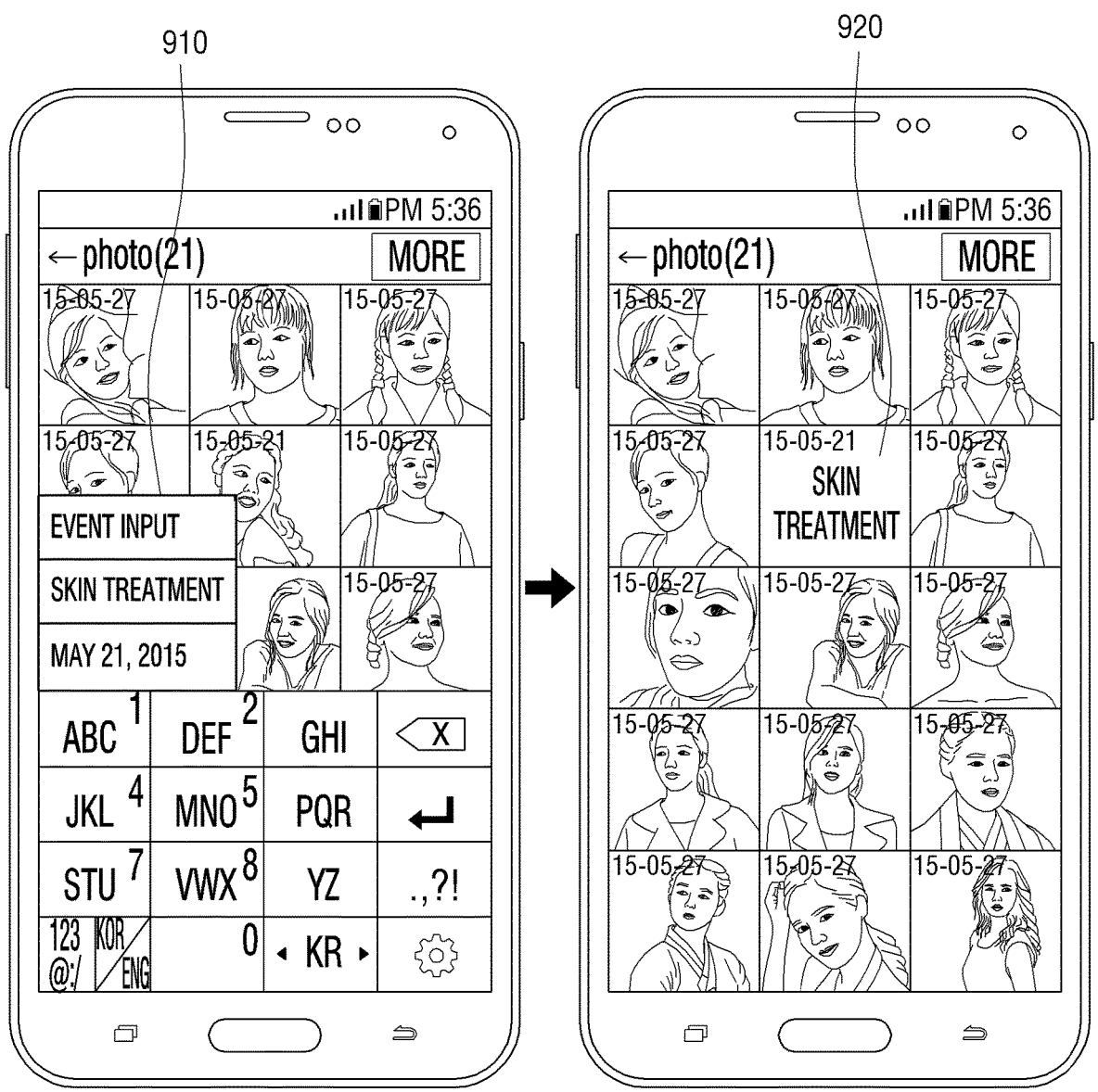
FIG. 9 is a diagram illustrating an example UI screen according to another example embodiment.

FIG. 9 is a diagram illustrating an example UI screen according to another example embodiment.

According to another example embodiment, UI screen in which a user can directly input the event on the gallery screen may be provided.

As illustrated, input window 910 for inputting the event may be provided on the gallery screen including the photo content according to the preset event. When the skin-related event is input on the input window 910, GUI 920 indicating the corresponding event as illustrated on the right side may be displayed between the photo content at real time. For example, when the skin treatment event is inputted at May 21", 2015, GUI 920 indicating the corresponding skin treatment event may be automatically added between the photos photographed before and after the corresponding skin treatment event.

Figure 10:
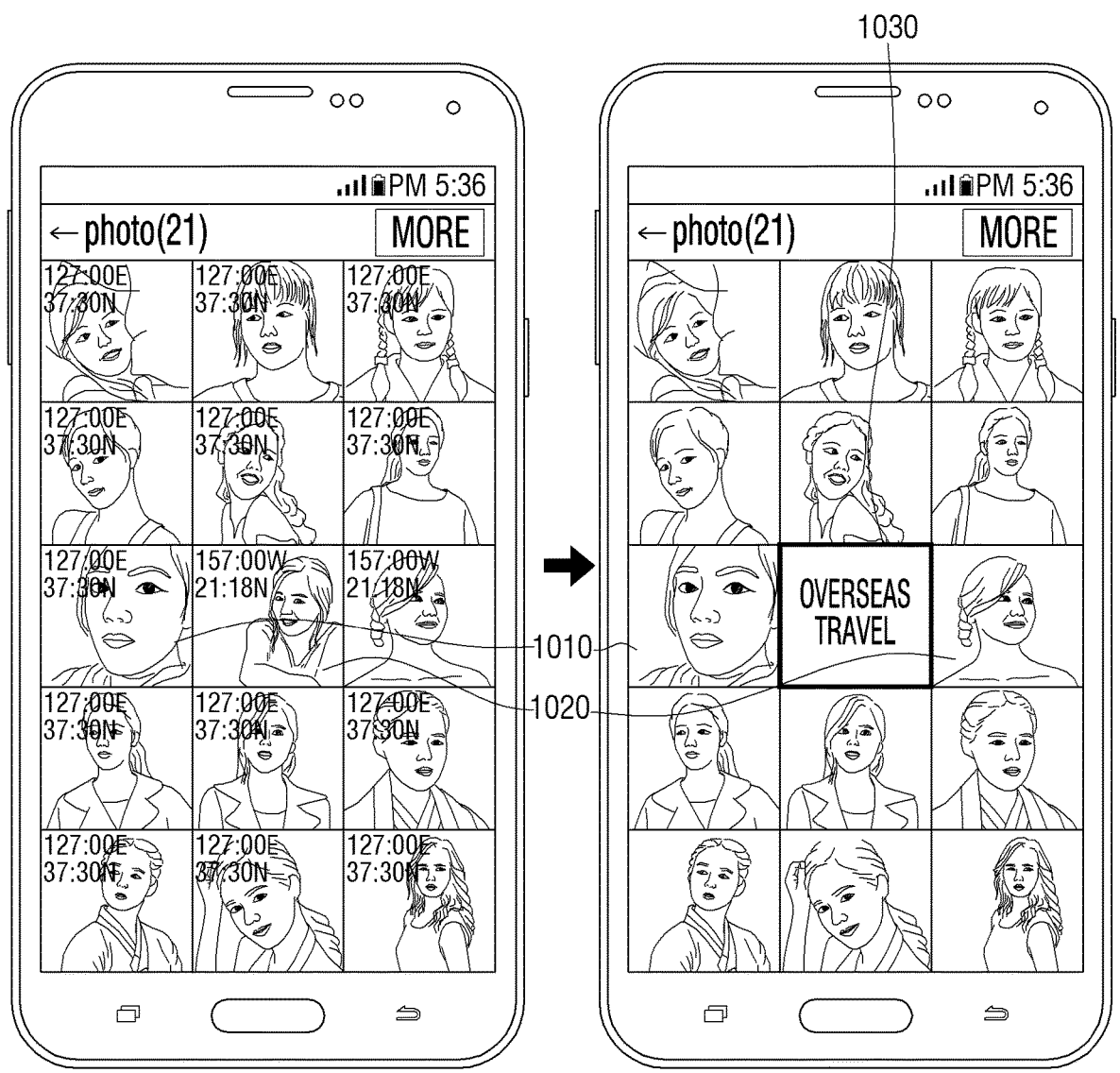
FIG. 10 is a diagram illustrating an example method for extracting a skin-related event based on GPS information according to another example embodiment.

FIG. 10 is a diagram illustrating an example method for extracting the skin-related event based on GPS information according to another example embodiment.

According to another example embodiment, the processor 120 may generate the skin-related event based on GPS information tagged with the photo content, e.g., based on the photographed position information.

As illustrated, the processor 120 may extract the event of a user visiting abroad based on GPS information tagged with the photo content provided based on the time order. For example, the processor 120 may determine that a user visited abroad at the corresponding time when the position information tagged with the photo content is modified to "157:00 W, 21:18 N" from "120:00 E, 37:30 N" at the specific time. In this case, GUI 1030 indicating the overseas trip event may be automatically added between the photo content 1010, 1020 corresponding to the time when the position information is modified.

However, using GPS information tagged with the photo content is merely one of many various example embodiments. The processor 120 may generate the event based on GPS information in which the moving position of the display apparatus 100 is recorded. For example, when the position of the display apparatus 100 is modified from "120:00 E, 37:30 N" to "157:00 W, 21:18 N" at specific time, the processor 120 may determine that a user visited abroad at the corresponding time. In this example, GUI indicating the corresponding event may be automatically added between the photo content corresponding to the time point.

Figure 11:
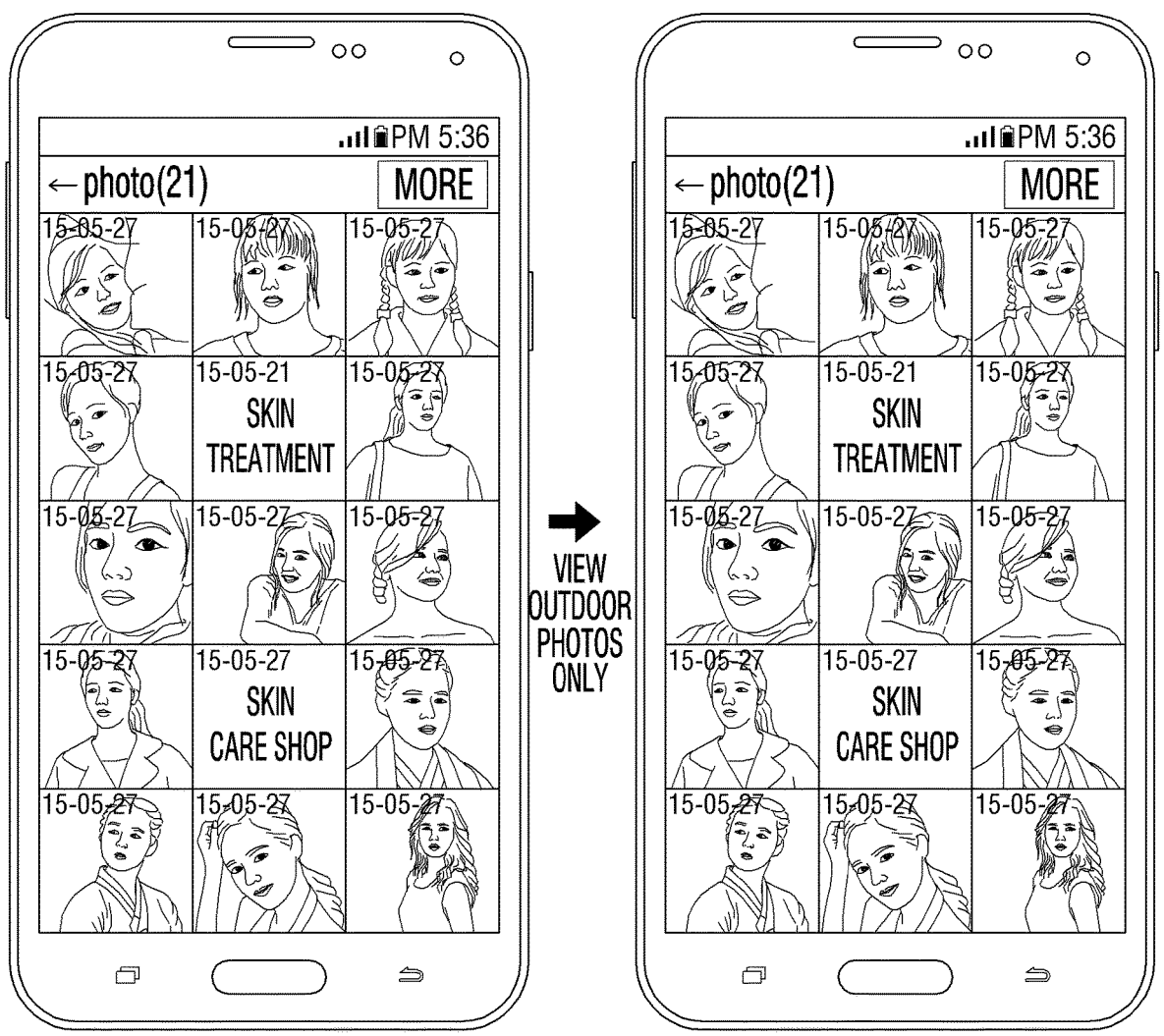
FIG. 11 is a diagram illustrating an example UI screen according to another example embodiment.

FIG. 11 is a diagram illustrating an example UI screen according to another example embodiment.

According to another example embodiment, the processor 120 may filter and provide only the photo content photographed internally or externally based on a user command.

For example, when a command of "view the outdoor photos only" is input on UI screen in which the photo content is distinguished and provided based on the skin-related event as illustrated, the processor 120 may filter and provide only the photo content photographed outdoor among the corresponding photo content. In this example, the processor 120 may distinguish and provide the photo content photographed outdoor based on the skin-related event.

The processor 120 may determine whether the photo content is photographed outdoors or indoors, by analyzing the photo content based on EXIF information tagged with the photo content. Thus, the processor 120 may determine whether the corresponding photo content are photo contents photographed outdoors or indoors based on the information such as aperture number and exposure correction number included in EXIF information.

The processor 120 may filter and provide the photo content based on various criteria based on a user command. For example, the processor 120 may filter and provide the photo content corresponding to a user command such as view only photo content in which the face size is equal to, or greater than a preset size or view only photo content in which the face is in forward direction.

Figure 12A:
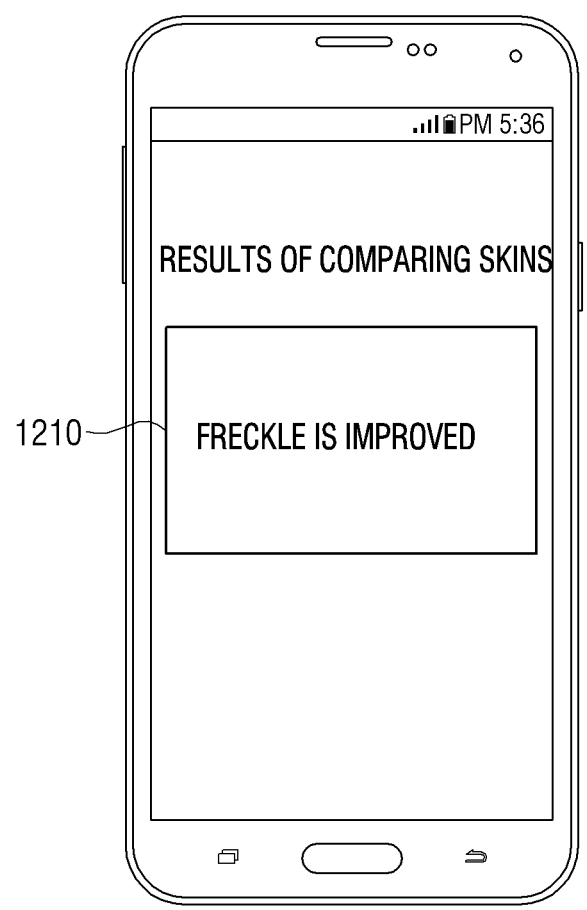
FIGS. 12A and 12B are diagrams illustrating an example method for providing the skin analysis results according to an example embodiment.
Figure 12B:
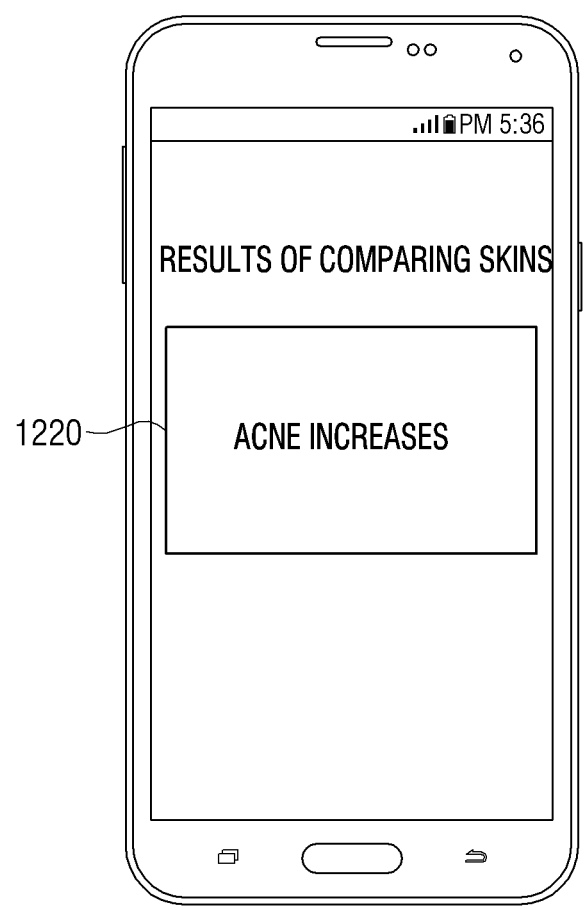

FIGS. 12A and 12B are diagrams illustrating an example method for providing the skin analysis results according to an example embodiment.

The results of comparing the skin conditions before and after the skin-related event according to an example embodiment may be briefly provided regarding the item under which the skin change is greatest. For example, when the freckle is obviously improved before and after the skin treatment compared to the other analyzing items, it may provide a message 1210 in the text form such as "the freckle is improved," as illustrated in FIG. 12A.

Further, when the acne clearly increases before and after the event such as overseas trip compared to the other analyzing items, it may provide a message 1220 in the text form such as "acne increases." Thus, even when a user is not accustomed to using a device, the user may recognize his or her skin change at a glance.

For example, UI screen illustrated in FIGS. 12A and 12B may be provided based on the preset event (e.g., input of a user command, elapse of the preset time) after UI screen 630 to compare the skin condition of the user face illustrated in the lower part of FIG. 6, or may be provided by substituting the corresponding UI screen 530.

Figure 13A:
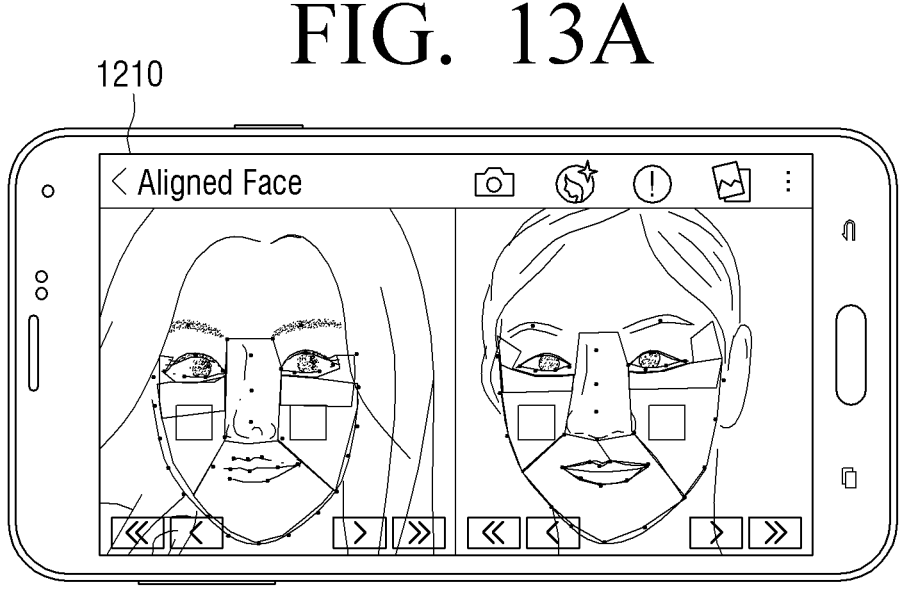
FIGS. 13A to 13C are diagrams illustrating an example method for providing the skin analysis results according to another example embodiment.
Figure 13A:
Figure 13A:
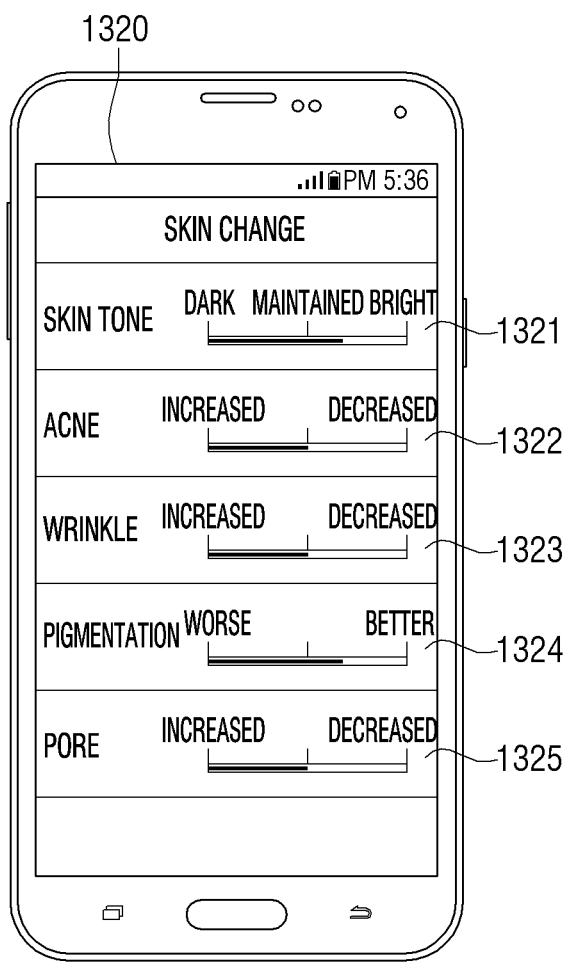
Figure 13B:
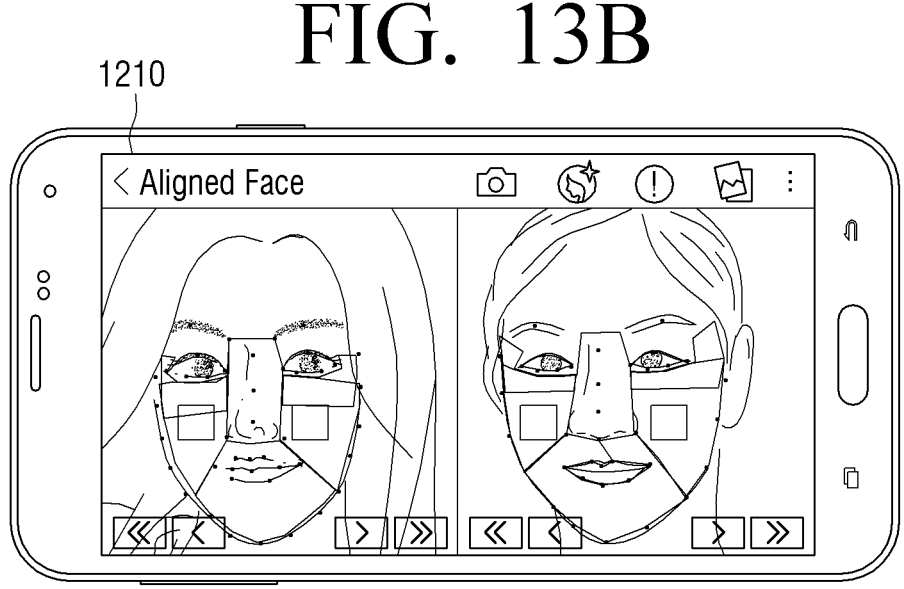
Figure 13B:
Figure 13B:
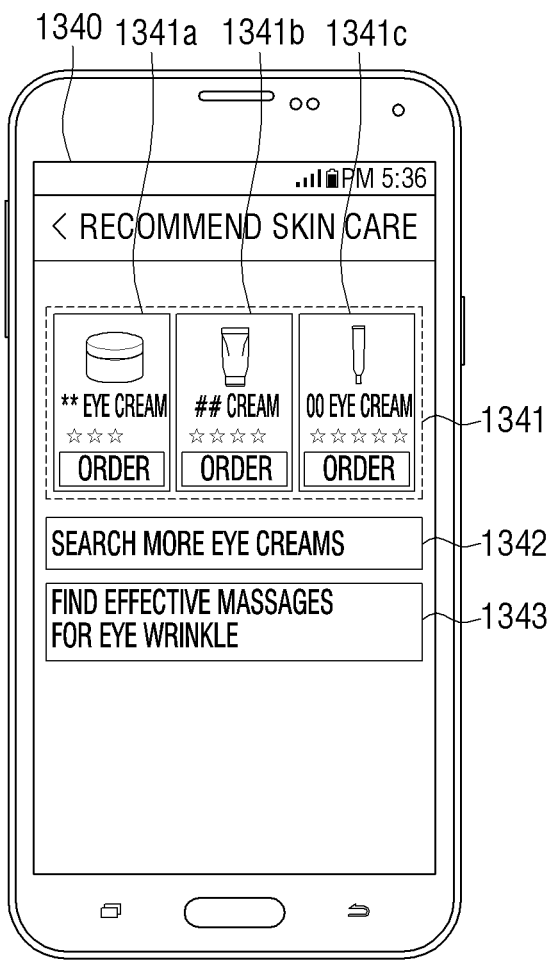
Figure 13C:
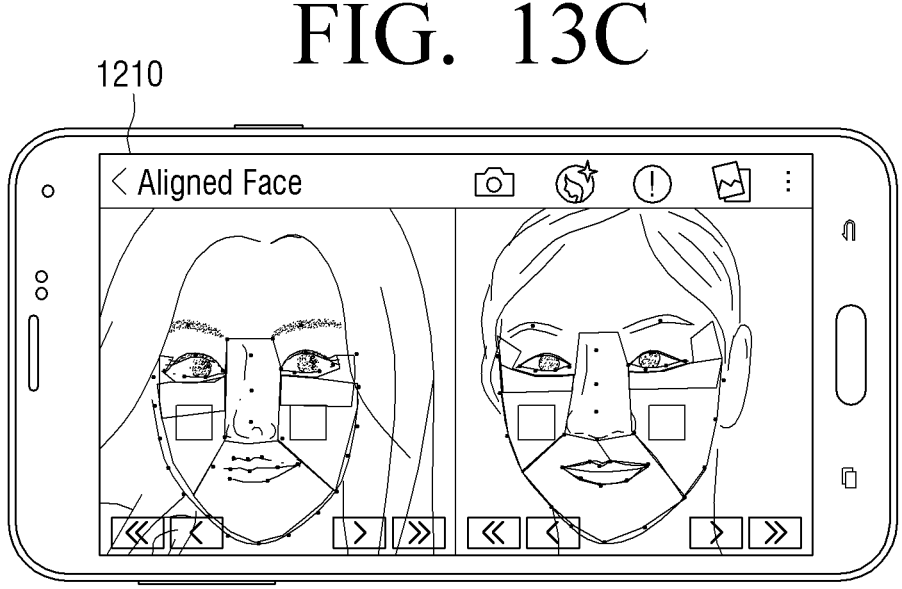
Figure 13C:
Figure 13C:
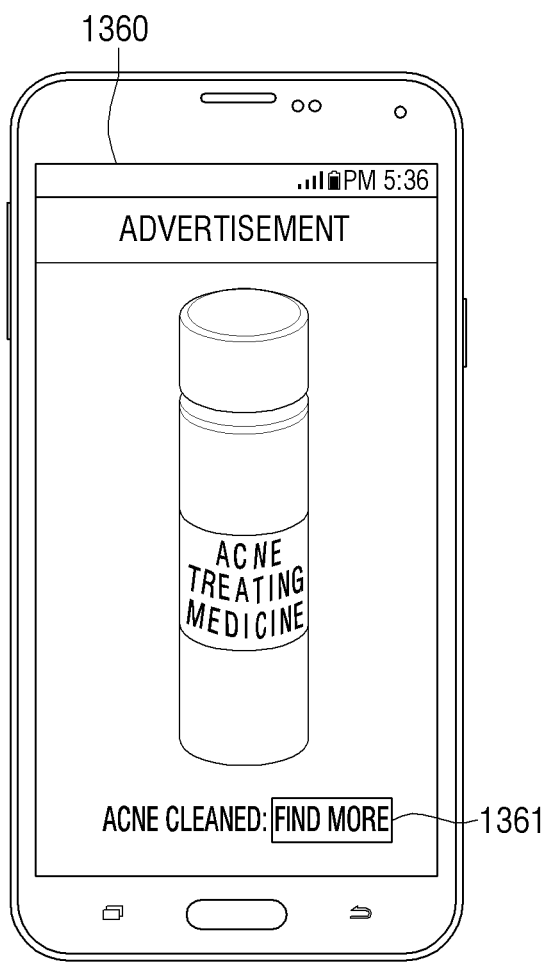

FIGS. 13A to 13C are diagrams illustrating an example method for providing the skin analysis results according to another example embodiment.

According to another example embodiment, the results of comparing the skin conditions before and after the skin-related event may be provided in detail per each analyzing item.

For example, when the preset event is input (e.g., user command, change of arrangement mode) on UI screen 1210 to compare the skin conditions before and after the skin-related event as illustrated in FIG. 13A, UI screen 1320 may be provided, indicating the skin change conditions before and after the event with various analyzing items such as skin tone 1321, acne 1322, wrinkle 1323, pigmentation 1324, and pore 1325.

According to yet another example embodiment, recommended skin care, recommended cosmetics information, and ads information regarding specific cosmetics may be provided according to the result of comparing the skin conditions before and after the skin-related event.

For example, when the preset event is input (e.g., user command, arrangement mode modification) on UI screen 1210 to compare the skin conditions before and after the skin-related event as illustrated in FIG. 13B, UI screen 1340 to provide the recommended skin care information according to the skin change conditions may be provided. For example, when the wrinkle surrounding the eyes considerably increases before and after the corresponding event, UI screen to include various recommend information for the eye care 1341, 1342, 1343 may be provided. For example, when the cosmetics for the eye care are recommended, UI screen may include items 1341a to 1341c to recommend the cosmetics based on the purchasing amount, the popularity rank, and the grade, or to directly link to the sites where the corresponding cosmetics can be purchased.

For another example, when the preset event is input (e.g., user command, arrangement mode modification) on UI screen 1210 to compare the skin conditions before and after the skin-related event as illustrated in FIG. 13C, UI screen 1360 may be provided to provide ads information regarding the specific cosmetics and the dermatology based on the skin change conditions. For example, when the acne considerably increases before and after the corresponding event, ads screen 1360 may be provided to advertise the products that can improve the acne. In this example, the ads screen 1360 may include a detail view button 1361 to convert into the ads regarding the acne treating medicine or the explanation screen regarding the acne treating medicine. For example, ads information may be provided based on a contract with the seller of the corresponding product and the contract with a specific dermatology.

FIGS. 14A, 14B, 15A and 15B are diagrams illustrating an example method for providing the skin analysis results according to another example embodiment.

According to another example embodiment, UI screen to compare the skin conditions before and after the skin-related event may be provided in various forms.

Figure 14A:
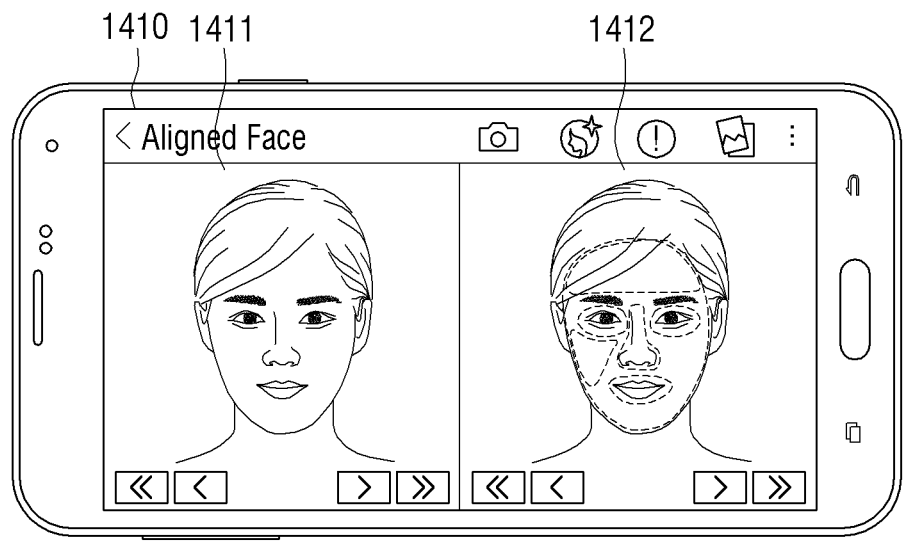
FIGS. 14A, 14B, 15A and 15B are diagrams illustrating an example method for providing the skin analysis results according to another example embodiment.
Figure 14B:
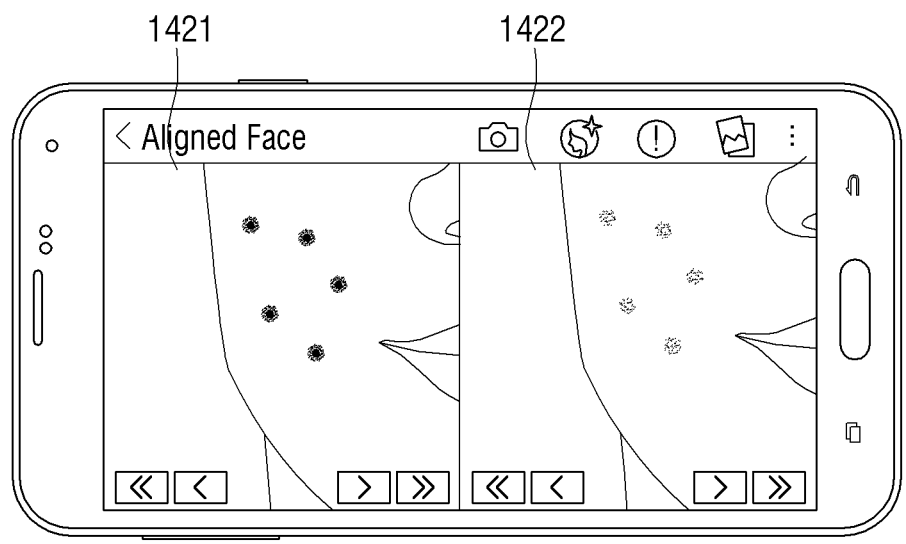

For example, after receiving a user command to select or magnify specific area (e.g., cheek area) from at least one of the corresponding photo content 1411, 1412 while providing UI screen 1410 including the photo content 1411, 1412 before and after the specific skin-related event as illustrated in FIG. 14A, the corresponding area may be magnified and displayed, or the content containing the corresponding area is photographed in detail may be newly displayed, as illustrated in FIG. 14B. In this example, the magnified or finely photographed content 1421, 1422 may include detail information regarding the corresponding area (e.g., a number of the acne, a color of the acne).

Figure 15A:
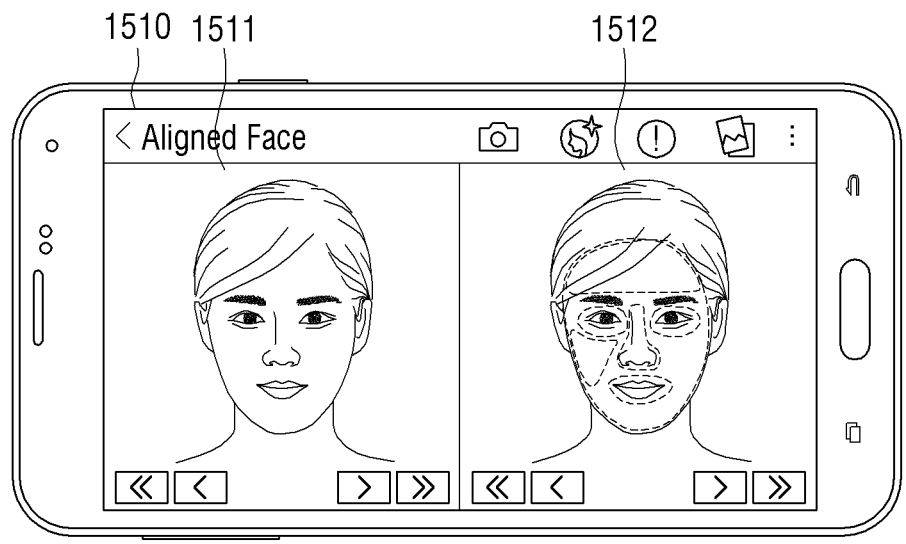
Figure 15B:
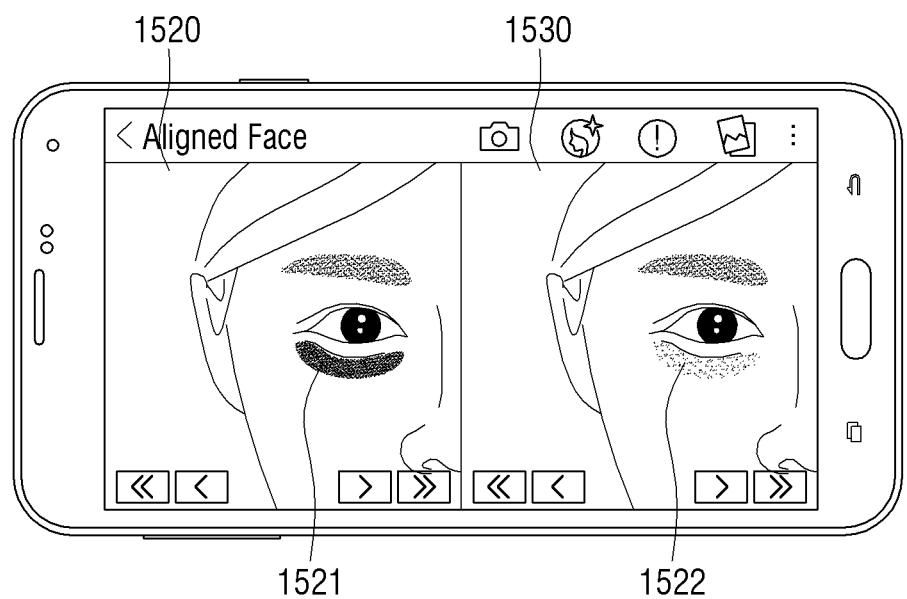

For another example, after receiving a user command to select or magnify the surrounding area of the eye from at least one of the corresponding photo content 1511, 1512 while providing UI screen 1510 including the photo content 1511, 1512 before and after the specific skin-related event as illustrated in FIG. 15A, the surrounding area of the eye may be magnified and provided or the content containing finely-photographed surrounding area of the eye 1520, 1530 may be newly displayed, as illustrated in FIG. 15B. In this example, the magnified or finely photographed content may include detail information regarding the surrounding area of the eye (e.g., a degree of the dark circle).

FIGS. 16A to 16C and 17 are diagrams illustrating an example UI provided in the preview screen according to various example embodiments.

Figure 16A:
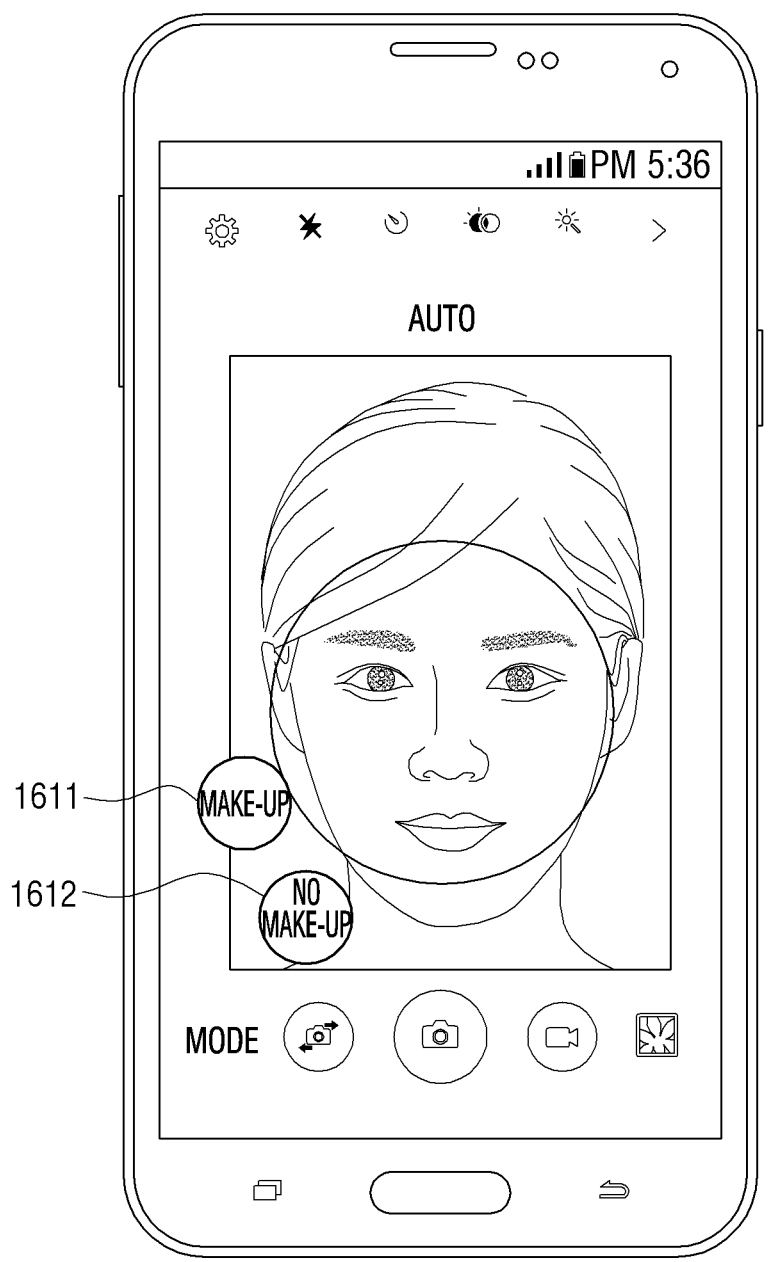
FIGS. 16A to 16C and 17 are diagrams illustrating an example UI provided on a preview screen according to various example embodiments.

FIG. 16A is a diagram illustrating the preview screen for the photographing or UI screen provided immediately after photographing while there is no previously registered user face picture.

For example, the processor 120 may provide the notification to ask whether or not the face included in the photographed image is a user face and to manage the skin change by comparing based on the above face. Further, when a user inputs a command to confirm the face, the processor 120 may register the corresponding face as user face and store as image for managing the skin analysis/change. A UI screen may provide UI buttons 1611, 1612 to select whether the face is with or without make-up, set the corresponding item as necessary item, or exclude the corresponding item from the necessary items when the user sets so.

Figure 16B:
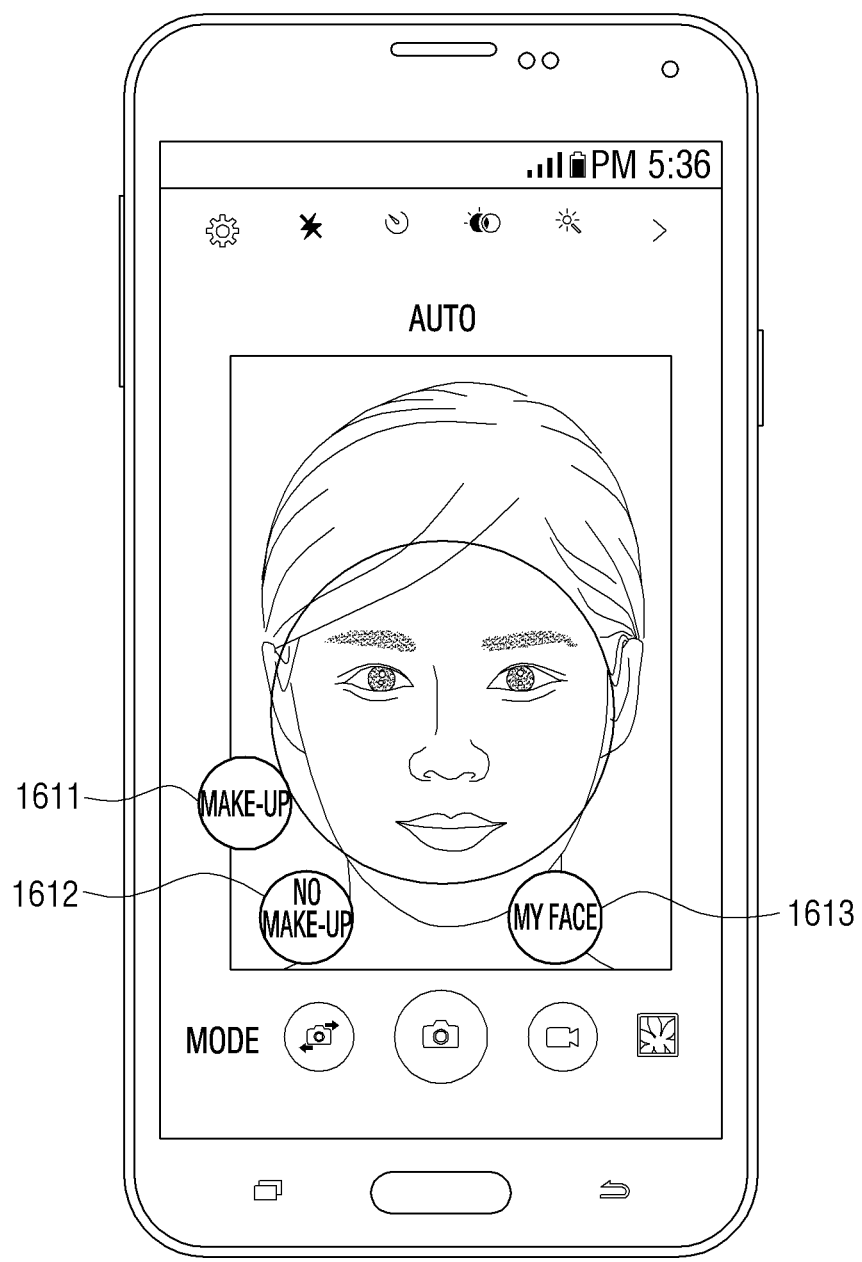

FIG. 16B is a diagram illustrating UI screen provided when the face included in the preview image or the photographed image does not match the user face which is previously registered.

For example, when one face detected from the preview screen does not match the registered user face, the processor 120 may additionally display UI button 1613 to confirm whether or not the detected face is a user face. In this example, the processor 120 may store the corresponding photo when the corresponding UI button 1613 is selected or store the corresponding photo for the skin analysis. According to various examples, the shutter button may be provided in an already-clicked state, in which case the photographing may be performed, only requiring clicking of the corresponding UI button 1613, e.g., without requiring a user to click the shutter button.

Figure 16C:
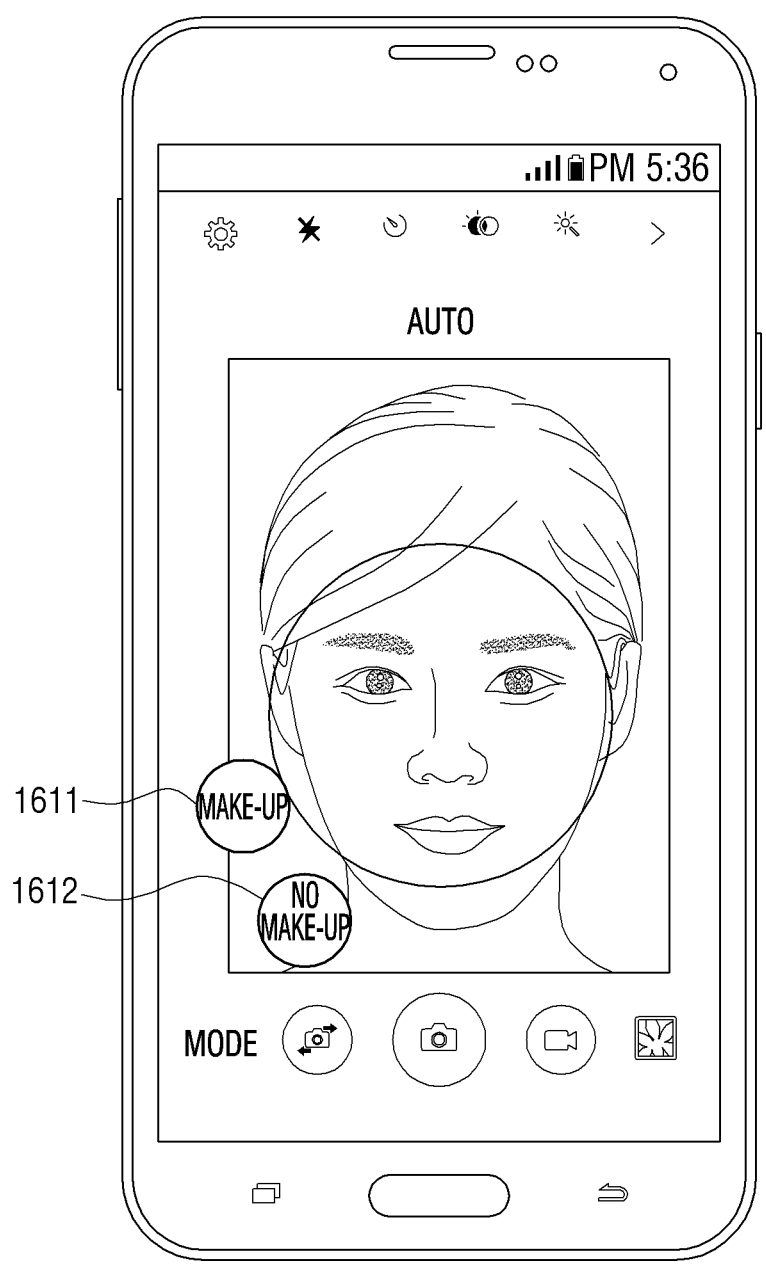

FIG. 16C is a diagram illustrating an example UI screen provided when the face included in the preview image or the photographed image matches the previously registered user face.

For example, the processor 120 may provide only UI buttons 1611, 1612 to select whether the face is with or without make-up, when the face detected from the preview screen matches the registered user face. According to various examples, the shutter button may be provided in an already-clicked state, in which photographing may be performed, only requiring clicking of the corresponding UI buttons 1611, 1612, e.g., without requiring a user to click the shutter button.

Figure 17:
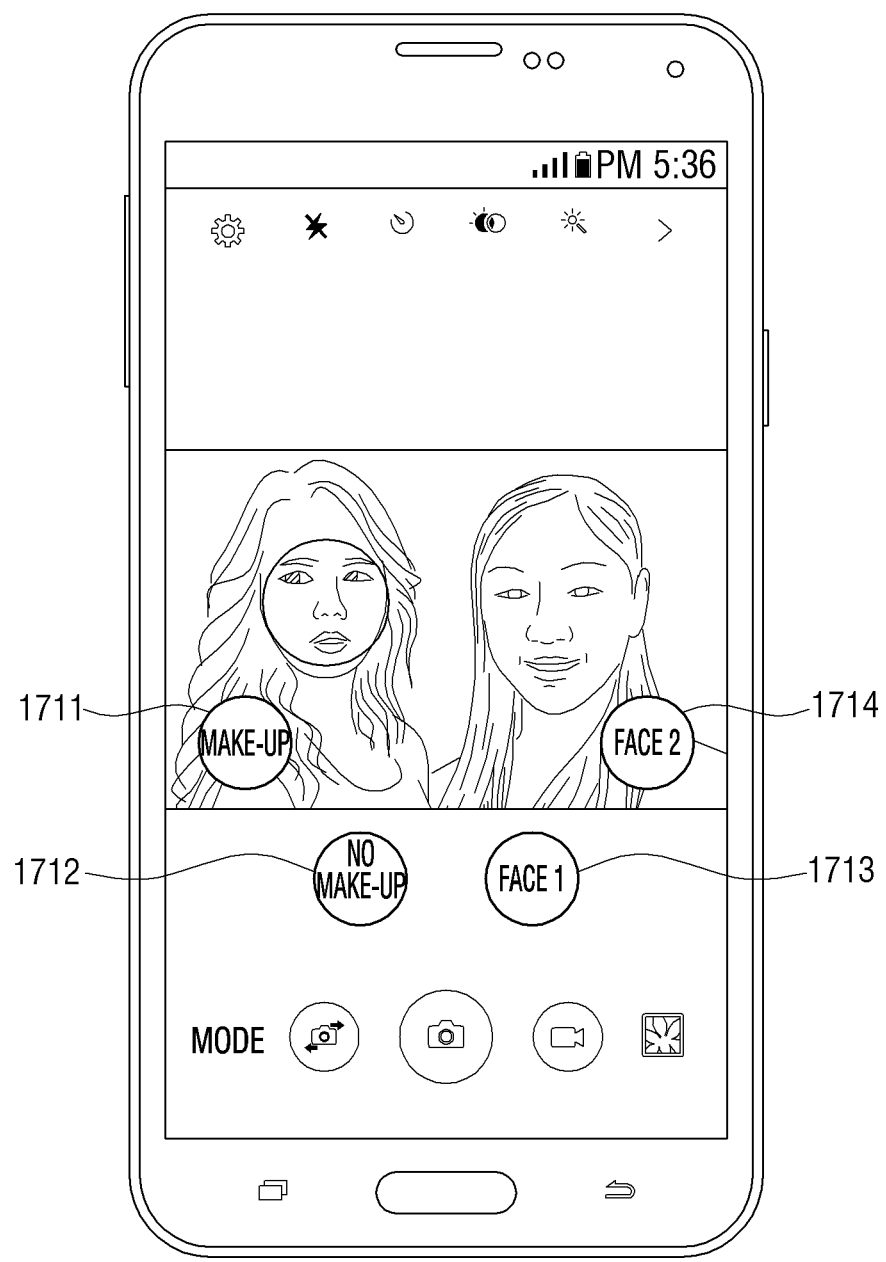

FIG. 17 is a diagram illustrating an example UI screen provided when a plurality of faces are detected from the preview image or the photographed image.

For example, the processor 120 may provide UI buttons 1711, 1712 to select whether the face that matches the registered user face is with or without make-up on the marked area, when a plurality of faces are detected from the preview screen and when one face matches the registered user face. According to various examples, the shutter button may be provided in an already-clicked state, in which case photographing may be performed, only requiring clicking of the corresponding UI buttons 1611, 1612, e.g., without requiring a user to click the shutter button.

When a plurality of faces are detected from the preview screen and when a plurality of faces do not match the registered user face, the processor 120 may additionally display UI buttons 1713, 1714 to select the user face.

When a plurality of faces are detected on the preview screen and when one face matches the registered user face, the processor 120 may display UI buttons 1713, 1714 to select the user face. In this example, one button among the corresponding buttons may be displayed in an already-clicked state, which may remove the need to separately select the corresponding buttons.

Figure 18:
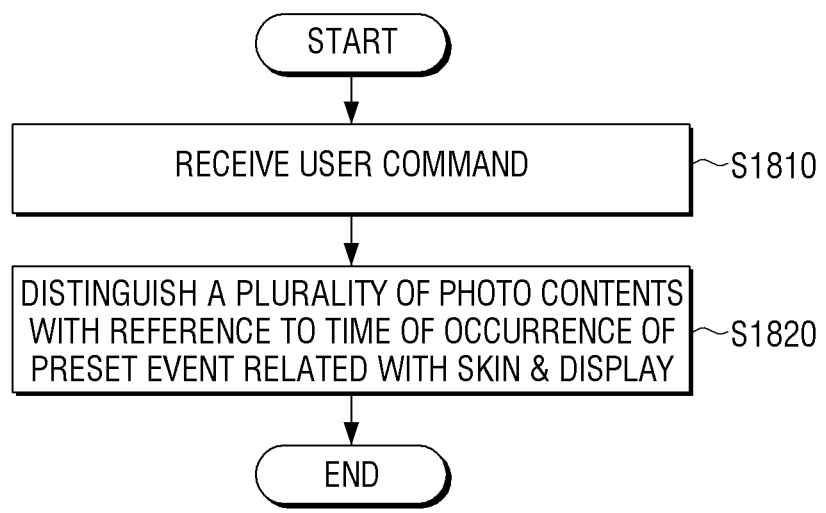
FIG. 18 is a flowchart illustrating an example method of controlling a display apparatus according to an example embodiment.

FIG. 18 is a flowchart illustrating an example method of controlling a display apparatus according to an example embodiment.

Regarding the control method of the display apparatus according to an example embodiment illustrated in FIG. 18, when a user command is received at S1810, a plurality of photo contents including the user face may be distinguishably displayed based on the photographing time point with reference to the time at which the skin-related preset event occurred at S1820.

Further, the method according to an example embodiment may include providing UI screen to compare the skin conditions of the user faces respectively included in the selected first and second photo content, when the first photo content is selected among the photo contents photographed before the time at which the preset event occurred and when the second photo content is selected among the photo contents photographed after the preset event occurred.

Further, at S1820, GUI indicating the preset event may be displayed between the photo content photographed before and after the time at which the preset event occurred such that a plurality of photo contents may be distinguishably displayed based on the time at which the preset event occurred.

Further, the method according to an example embodiment may include selecting the third photo content among the photo contents photographed before the time at which the preset event occurred, when GUI is selected based on the user command, selecting the second photo content having the similar photographing conditions to the fourth photo content among the photo contents photographed after the time at which the preset event occurred, and providing UI screen to compare the skin conditions of the user faces respectively included in the selected third and fourth photo content.

The photographing condition may include at least one among the user face size, the user face angle, the photographing lighting, whether the face is with or without make-up, and presence or absence of accessory.

The preset event related with skin may include at least one among the skin care event, the skin treatment event, the product purchasing event related with skin, the event related with the change of location influencing the skin, the event related with the weather influencing the skin, the event related with the food consumption influencing the skin, and the holiday event.

The method according to an example embodiment may include a process for determining the preset event based on at least one among the skin-related event input on the preset calendar, the skin-related event included in a text message, GPS information, and the food-related information input by a user or included in the photo content.

Further, at S1820, the operation may involve filtering only the skin-analyzed photo content, and distinguishably displaying the photo content with reference to the time at which the preset event related with skin care occurred, when the skin mode is selected on the gallery screen including a plurality of photo contents.

Operation at S1820 may involve adding GUI to the skin-analyzed photo content to identify the skin-analyzed photo content from the rest of the plurality of photo contents on the gallery screen.

The method according to an example embodiment may further include displaying at least one of a menu button regarding matching or non-matching the previously registered user face and a menu button regarding make-up or no make-up, when at least one face is detected from the preview screen for the photographing.

Figure 19:
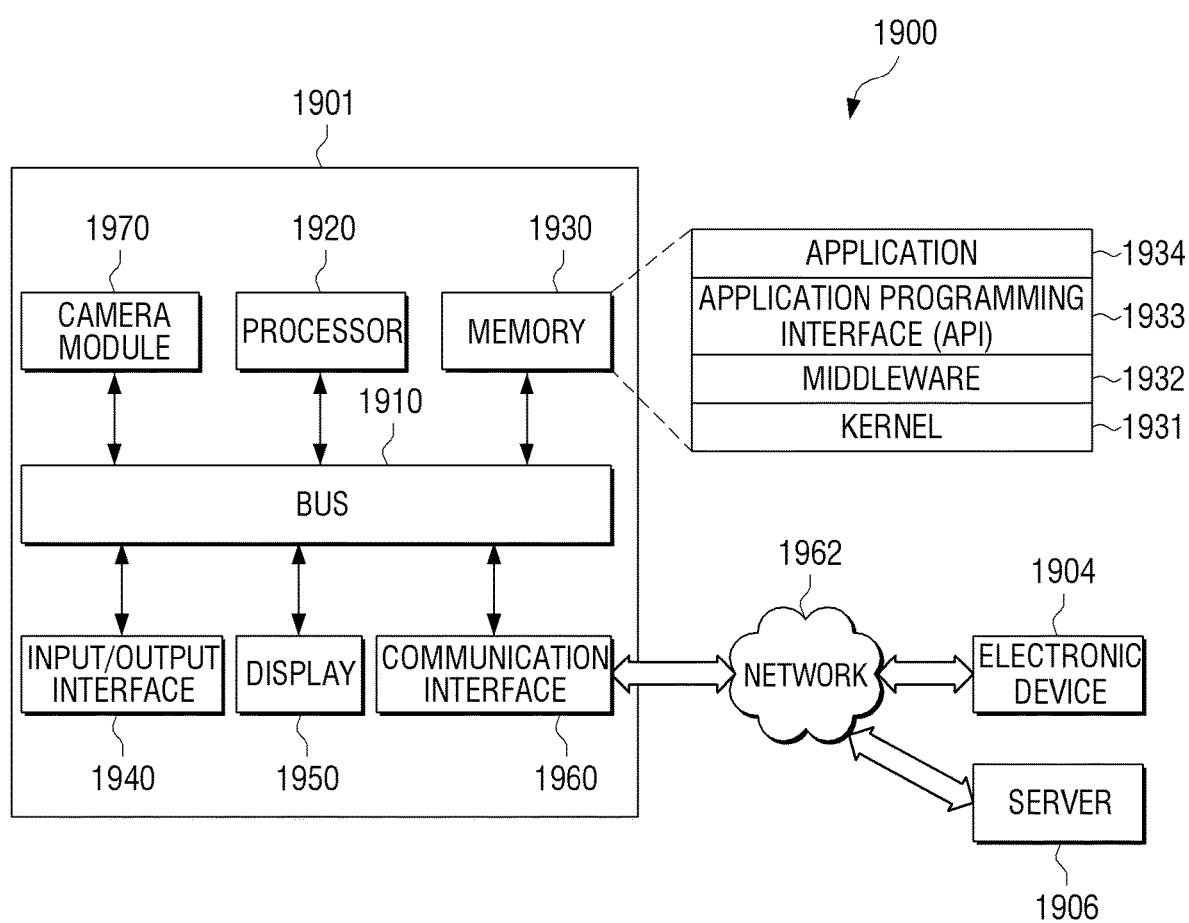
FIG. 19 is a diagram illustrating an example of a network environment according to various example embodiments.

FIG. 19 is a diagram illustrating an example embodiment of the network environment according to various example embodiments.

Referring to FIG. 19, the network environment 1900 according to an example embodiment may include at least one of the display apparatuses 1901, 1904 and the server 1906; at least one of the display apparatuses 1901, 1904 and the server 1906 may be connected to each other through the network 1962.

The display apparatus 1901 may include the bus 1910, the processor 1920, the memory 1930, the input/output interface 1940, the display 1950, the communication interface 1960 and the camera module 1970. The bus 1910 may include circuits to connect the elements described above to each other and deliver the communication (e.g., control message) between the elements described above. The processor 1920 may receive a command from the other elements described above (e.g., memory 1930, input/output interface 1940, display 1950, communication interface 1960, or camera module 1970) through the bus 1910, decrypt the received command, and perform calculation or data processing according to the decrypted command.

The processor 1920 may control overall operation of the display apparatus 1901. According to the various embodiments, the processor 1920 may include at least one processor (e.g., processor 120 of FIG. 2A).

The memory 1930 may store commands or data received from the processor 1920 or the other elements or generated with the processor 1920 or the other elements. For example, the memory 1930 may include programming module such as kernel 1931, middleware 1932, application programming interface (API) 1933, or application 1934. The above described programming module may be configured to be software, firmware, hardware, or combination of at least two among the above.

The kernel 1931 may control or manage the system resources (e.g., bus 1910, processor 1920 or memory 1930) used in performing the operation or the function which is implemented on the other programming module, e.g., the middleware 1932, API 1933 or the application 1934. Further, the kernel 1931 may provide the interface to access and control or manage each unit of the display apparatus 1901 by the middleware 1932, API 1933 or the application 1934.

The middleware 1932 may perform the mediating role such that API 1933 or the application 1934 can exchange the data by communicating with the kernel 1931. Further, regarding the job requests received from the application 1934, the middleware 1932 may perform the control of the job requests (e.g., scheduling or load balancing) by using a method for allocating the priority to use the system resources (e.g., bus 1910, processor 1920, or memory 1930) of the display apparatus 1901 on at least one application among the application 1934.

API 1933 may be interface in which the application 1934 controls the functions provided from the kernel 1931 or the middleware 1932. For example, API 1933 may include at least one interface or mathematical function (e.g., instructions) for the file control, the window control, the image processing or the character control.

According to the various example embodiments, the application 1934 may include SMS/MMS application, the calendar application, the alarm application, the e-mail application, the health care application (e.g., application to measure the exercising amount or the blood sugar), or the environment information application (e.g., application to provide information regarding the pressure, the humidity or the temperature), etc. Additionally or alternatively, the application 1934 may be application related with the information exchange between the display apparatus 1901 and the external electronic device (e.g., display apparatus 1904), or the like. The application related with the information exchange may include the notification relay application to deliver the specific information to the above external electronic device or the device management application to manage the above external electronic device. According to various examples, the application 1934 may include the application which is separately manufactured to provide the skin care and analyzing service according to an embodiment.

The input/output interface 1940 may deliver the commands or data input from a user through an input/output device (e.g., sensor, keyboard or touch screen) to the processor 1920, the memory 1930, the communication interface 1960 or the camera module 1970 through the bus 1910. For example, the input/output interface 1940 may provide the data regarding the user touch inputted through the touch screen to the processor 1920. The input/output interface 1940 may output the commands or data, which are received from the processor 1920, the memory 1930, the communication interface 1960, or the camera module 1970 through the bus 1910, with the input/output device (e.g., speaker or display). For example, the input/output interface 1940 may output the voice data processed through the processor 1920 to a user with the speaker. The display 1950 may display various pieces of information to a user (e.g., multimedia data or text data). The communication interface 1960 may connect the communication between the display apparatus 1901 and the external device (e.g., display apparatus 1904 or server 1906). For example, the communication interface 1960 may communicate with the above external device by being connected to the network 1962 through the wireless communication or the wire communication. The above wireless communication may include at least one among wireless fidelity (WiFi), Bluetooth (BT), near field communication (NFC), global positioning system (GPS) or the cellular communication (e.g., LTE, LTE-A, CDMA, WCDMA, UMTS, WiBro or GSM). The wire communication may include at least one among universal serial bus (USB), high definition multimedia interface (HDMI), recommended standard 232 (RS-232) or plain old telephone service (POTS).

The camera module 1970 may be controlled with the information obtained from the other elements (e.g., processor 1920, memory 1930, input/output interface 1940, or communication interface 1960). Thus, the camera module 1970 may magnify or photograph specific area in detail by zooming in the photographed image.

According to an example embodiment, the network 1962 may be telecommunication network. The telecommunication network may include at least one among the computer network, the internet, the internet of things or the telephone network, or the like. According to an example embodiment, the protocol for the communication between the display apparatus 1901 and the external device (e.g., transport layer protocol, data link layer protocol or physical layer protocol) may be supported from at least one among the application 1934, API 1933, the middleware 1932, the kernel 1931 or the communication interface 1960.

At least part of the apparatus (module or their functions) or the method (e.g., operations) according to the various example embodiments may be implemented as instructions stored in computer-readable storage media that can be read by a computer in a form of the programming module. When the instructions are performed by at least one processor (or controller), at least one processor may perform the functions corresponding to the instructions. The computer-readable storage media that can be read by a computer may be storage or memory. At least part of the programming module may be implemented by the processor. At least part of the programming module may include module, programs, routines, sets of instructions or processes to perform at least one function.

The computer readable storage media may include the magnetic media such as hard disc, floppy disc, and magnetic tape, the optical media such as CD-ROM (compact disc read only memory) and DVD (digital versatile disc), the magneto-optical media such as floptical disc, and the hardware device configured to store and perform the program instructions (e.g., programming module) such as ROM, RAM and flash memory. Further, the program instructions may include high language codes that can be performed by a computer with the interpreter as well as mechanical codes which are generated by the compiler. The above described hardware device may be configured to operate as at least one software module to perform the operations of the various embodiments, and vice versa.

Regarding the module or the programming module according to the various example embodiments, at least one among the elements described above may be included, some elements may be deleted, or other additional new elements may be further included. The operations performed with the module, the programming module or the other elements according to the various example embodiments may be performed with the sequential, the parallel, the repetitive, or the heuristic method. Further, some operations may be performed in a different order or deleted, and other new operations may be added.

According to the various example embodiments, regarding the computer readable storage media to store the instructions, the instructions may be set to perform at least one operation with at least one processor when being performed with at least one processor.

Further, the example embodiments illustrated and described in the disclosure and the drawings are merely provided to explain the technical essence of the disclosure more easily and to support the understanding of the various example embodiments, but may not limit the scope of the disclosure. According to the various example embodiments, regarding the computer readable storage media to store the instructions, the instructions are set to perform at least one operation with at least one processor when being performed with at least one processor. At least one operation may include the distinguishing and the displaying a plurality of photo contents including the user face based on the photographing time with reference to the time at which the preset event related with skin occurred, when a user command is received.

The foregoing example embodiments and advantages are merely examples and are not to be construed as limiting the example embodiments. The disclosure can be readily applied to other types of apparatuses. Also, the description of the example embodiments of the disclosure is intended to be illustrative, and not to limit the scope of the claims.

What is claimed is:
1. A display apparatus, comprising:
   a display; and
   a processor configured to:
      control the display to display a screen comprising a plurality of photo contents including a user face, based on at least one of a skin analysis application and a skin item being selected by a user input, control the display to display-skin-analyzed photo contents from among the plurality of photo contents, control the display to distinguishably display at least one of skin-analyzed photo content photographed before a predetermined event related with skin care and at least one of skin-analyzed photo content photographed after the predetermined event, based on user selection of a first photo content from among the at least one of skin-analyzed photo content photographed before the predetermined event, identify a second photo content having a same photographing condition as the first photo content from among the at least one of skin-analyzed photo content photographed after the predetermined event, and control the display to display a screen to compare a first skin condition of the user face included in the first photo content and a second skin condition of the user face included in the second photo content, wherein the display-skin-analyzed photo contents include photographing time information, and wherein the processor is further configured to:

obtain time information corresponding to the predetermined event, and identify the first photo content and second photo content based on the photographing time information and the time information corresponding to the predetermined event.

2. The display apparatus of claim 1, wherein the processor is configured to display a graphic user interface (GUI) displaying an indication of the predetermined event between the skin-analyzed photo contents photographed before and after a time at which the predetermined event occurred and to distinguishably display the plurality of photo contents with reference to the time at which the predetermined event occurred.

3. The display apparatus of claim 2, further comprising: a user interface configured to receive a user command, wherein, the processor is configured to select a third photo content from among the photo contents photographed before the time at which the predetermined event occurred, to select a fourth photo content having a photographing condition similar to that of the third photo content from among the photo contents photographed after the time at which the predetermined event occurred, and to provide a UI screen to compare the skin conditions of the user faces respectively included in the selected third and fourth photo content when the GUI is selected based on the user command.

4. The display apparatus of claim 3, wherein the photographing condition includes at least one of a user face size, a user face angle, a user face expression, make-up or no make-up, presence or absence of an accessory, and photographing lighting.

5. The display apparatus of claim 1, wherein the predetermined event related with skin care includes at least one of a skin care event, a skin treatment event, a product purchasing event related with skin, an event related with a change of location influencing the skin, an event related with weather influencing the skin, an event related with food consumption influencing the skin, and a holiday event.

6. The display apparatus of claim 1, wherein the processor is configured to determine the predetermined event based on at least one of a skin-related event input on a predetermined calendar, a skin-related event included in a text message, GPS information, and food-related information included in a photo content or input.

7. The display apparatus of claim 1, wherein the processor is configured to display the skin-analyzed photo contents with reference to a time at which the predetermined event related with skin care occurred when the skin mode is selected on a gallery screen comprising the plurality of photo contents.

8. The display apparatus of claim 7, wherein the processor is configured to add a graphic user interface (GUI) to the skin-analyzed photo content to identify the skin-analyzed photo content from a remaining portion of the plurality of photo contents on the gallery screen and to display the result.

9. The display apparatus of claim 1, wherein, the processor is configured to display at least one of a menu button regarding match or non-match with a previously registered user face, and a menu button regarding make-up or no make-up when at least one face is identified from a preview screen provided for photographing.

10. A method of controlling a display apparatus, comprising:

based on a user command selecting at least one of a skin analysis application and a skin item being received, displaying skin-analyzed photo contents from among a plurality of photo contents; and based on the receiving the user command, distinguishably displaying at least one of skin-analyzed photo content including a user face photographed before a predetermined event related with skin care and at least one of skin-analyzed photo content photographed after the predetermined event, wherein the distinguishably displaying comprises:

based on user selection of a first photo content from among the at least one of skin-analyzed photo content photographed before the predetermined event, identifying a second photo content having a same photographing condition as the first photo content from among the at least one of skin-analyzed photo content photographed after the predetermined event, displaying a screen to compare a first skin condition of the user face included in the first photo content and a second skin condition of the user face included in the second photo content, wherein the display-skin-analyzed photo contents include photographing time information, obtaining time information corresponding to the predetermined event, and identifying the first photo content and second photo content based on the photographing time information and the time information corresponding to the predetermined event.

11. The method of claim 10, wherein the displaying comprises displaying a graphic user interface (GUI) providing an indication of the predetermined event between the skin-analyzed photo contents photographed before and after a time at which the predetermined event occurred, such that the plurality of skin-analyzed photo contents are distinguishably displayed with reference to the time at which the predetermined event occurred.

12. The method of claim 11, wherein when the GUI is selected based on the received user command, the method further comprises selecting a third photo content from among the photo contents photographed before the time at which the predetermined event occurred, and selecting a fourth photo content having the photographing condition similar to that of the third photo content from among the photo contents photographed after the time at which the predetermined event occurred, and providing a UI screen to compare the skin conditions of the user faces respectively included in the selected third and fourth photo content.

13. The method of claim 12, wherein the photographing condition includes at least one of a user face size, a user face angle, a user face expression, make-up or no make-up, presence or absence of accessory, and a photographing lighting.

14. The method of claim 10, wherein the predetermined event includes at least one of a skin care event, a skin treatment event, a product purchasing event related with skin, an event related with a change of location influencing the skin, an event related with weather influencing the skin, an event related with food consumption influencing the skin, and a holiday event.

15. The method of claim 10, further comprising determining the predetermined event based on at least one of a skin-related event input on a predetermined calendar, a skin-related event included in a text message, GPS information, and food-related information included in a photo content or input.

16. The method of claim 10, further comprising distinguishably displaying the skin-analyzed photo content with reference to a time at which the predetermined event related with skin care occurred when the skin mode is selected on a gallery screen comprising a plurality of photo contents including both skin-analyzed and non-skin analyzed photo contents.

17. The method of claim 16, further comprising adding a graphic user interface (GUI) to the skin-analyzed photo content to identify the skin-analyzed photo content from a remaining portion of the plurality of photo contents on the gallery screen and to display the result.

18. The method of claim 10, further comprising displaying at least one of a menu button regarding match or non-match with a previously registered user face, and a menu button regarding make-up or no make-up when at least one face is identified from a preview screen provided for photographing.

* * * * *